United States Patent
Carrera Fabra et al.

(10) Patent No.: US 9,304,066 B2
(45) Date of Patent: Apr. 5, 2016

(54) FLUIDICALLY INTEGRATED ROTARY BEAD BEADER

(71) Applicant: STAT-DIAGNOSTICA & INNOVATION, S.L., Barcelona (ES)

(72) Inventors: Jordi Carrera Fabra, Barcelona (ES); Anna Comengés Casas, Barcelona (ES); Ricard Martín Blanco, Barcelona (ES); Rafael Bru Gibert, Barcelona (ES)

(73) Assignee: Stat-Diagnostica & Innovation S.L., Barcelona (ES)

( * ) Notice: Subject to any disclaimer, the term of this patent is extended or adjusted under 35 U.S.C. 154(b) by 105 days.

(21) Appl. No.: 13/836,741

(22) Filed: Mar. 15, 2013

(65) Prior Publication Data

US 2013/0280710 A1     Oct. 24, 2013

Related U.S. Application Data

(60) Provisional application No. 61/622,858, filed on Apr. 11, 2012.

(51) Int. Cl.
*B02C 17/16* (2006.01)
*G01N 1/28* (2006.01)
(Continued)

(52) U.S. Cl.
CPC .............. *G01N 1/28* (2013.01); *B01F 7/00116* (2013.01); *B01F 7/00216* (2013.01);
(Continued)

(58) Field of Classification Search
CPC .......... G01N 1/28; G01N 1/286; B02C 19/00; B02C 17/16; B02C 17/163; B02C 17/1815; B02C 17/186; C12M 47/06; B01F 7/00941; B01F 7/00491; B01F 7/00258; B01F 7/00216; B01F 13/104; C12N 1/066

USPC ........................................ 241/2, 23, 65, 172
See application file for complete search history.

(56) References Cited

U.S. PATENT DOCUMENTS 3,993,254 A    11/1976   Bicik et al.
4,856,717 A     8/1989   Kamiwano et al.
(Continued)

FOREIGN PATENT DOCUMENTS

| | | |
|---|---|---|
| CN | 2250810 Y | 4/1997 |
| JP | S5060863 A | 5/1975 |
| JP | H0598589 A | 4/1993 |

OTHER PUBLICATIONS

International Search Report for International Application No. PCT/EP2013/057625, European Patent Office, Netherlands, mailed on Sep. 23, 2013.
(Continued)

*Primary Examiner* — Mark Rosenbaum
(74) *Attorney, Agent, or Firm* — Sterne, Kessler, Goldstein & Fox P.L.L.C.

(57) ABSTRACT

A system for at least one of homogenization and lysis of a sample includes one or more walls forming an enclosed chamber having an inlet and a plurality of fluidic connections. A first fluidic network is coupled to at least one of the plurality of fluidic connections and a second fluidic network is coupled to at least one of the plurality of fluidic connections. The system further includes a rotary element within the chamber, and an actuator configured to rotate the rotary element. The first fluidic network is configured to introduce at least a sample into the chamber from at least one first reservoir. The second fluidic network is configured to expel at least the sample from the chamber to at least one second reservoir. The rotary element is rotated by the actuator about an axis extending along a length of the rotary element.

61 Claims, 19 Drawing Sheets

(51) Int. Cl.
    *B01F 7/00*     (2006.01)
    *B01F 13/10*     (2006.01)
    *C12N 1/06*     (2006.01)
    *C12M 1/00*     (2006.01)
    *B01L 3/00*     (2006.01)

(52) U.S. Cl.
    CPC ........ *B01F 7/00258* (2013.01); *B01F 7/00291* (2013.01); *B01F 7/00491* (2013.01); *B01F 7/00941* (2013.01); *B01F 13/1044* (2013.01); *B02C 17/16* (2013.01); *C12M 47/06* (2013.01); *C12N 1/066* (2013.01); *G01N 1/286* (2013.01); *B01F 2013/1086* (2013.01); *B01L 3/502* (2013.01); *G01N 2001/2866* (2013.01)

(56) References Cited

U.S. PATENT DOCUMENTS

| | | | |
|---|---|---|---|
| 5,074,474 A * | 12/1991 | Golz et al. .......................... 241/1 |
| 5,269,470 A | 12/1993 | Ishikawa et al. |
| 5,346,146 A | 9/1994 | Nitta |
| 5,464,163 A | 11/1995 | Zoz |
| 5,593,097 A | 1/1997 | Corbin |
| 5,678,776 A | 10/1997 | Zoz |
| 5,934,579 A | 8/1999 | Hiersche et al. |
| 5,934,581 A | 8/1999 | Chiappa |
| 6,019,300 A | 2/2000 | Zoz |
| 6,029,920 A | 2/2000 | Shimizu et al. |
| 6,235,501 B1 * | 5/2001 | Gautsch et al. ............. 435/91.1 |
| 6,942,169 B2 * | 9/2005 | Sparks ............................. 241/1 |
| 2004/0200909 A1 | 10/2004 | McMillan et al. |
| 2010/0009349 A1 * | 1/2010 | Hollander ........................ 435/6 |
| 2010/0331522 A1 | 12/2010 | Irvine et al. |
| 2011/0070589 A1 | 3/2011 | Belgrader et al. |

OTHER PUBLICATIONS

Middelberg, Anton P.J., "Process-Scale Disruption of Microorganisms," Biotechnology Advances, vol. 13, No. 3, pp. 491-551, 1995.
Chisti, Y. et al., "Disruption of Microbial Cells for Intracellular Products," Enzyme Microb. Technol. vol. 8, pp. 194-204, Apr. 1986.
Office Action mailed Apr. 6, 2015, in Japanese Patent Application No. 2015-504957, Carrera Fabra, et al., filed Apr. 11, 2013.
Chinese Office Action directed to App. No. CN 201380026996.7, mailed Dec. 3, 2015; 12 pages.
English Translation of Chinese Office Action directed to App. No. CN 201380026996.7, mailed Dec. 3, 2015; 11 pages.

* cited by examiner

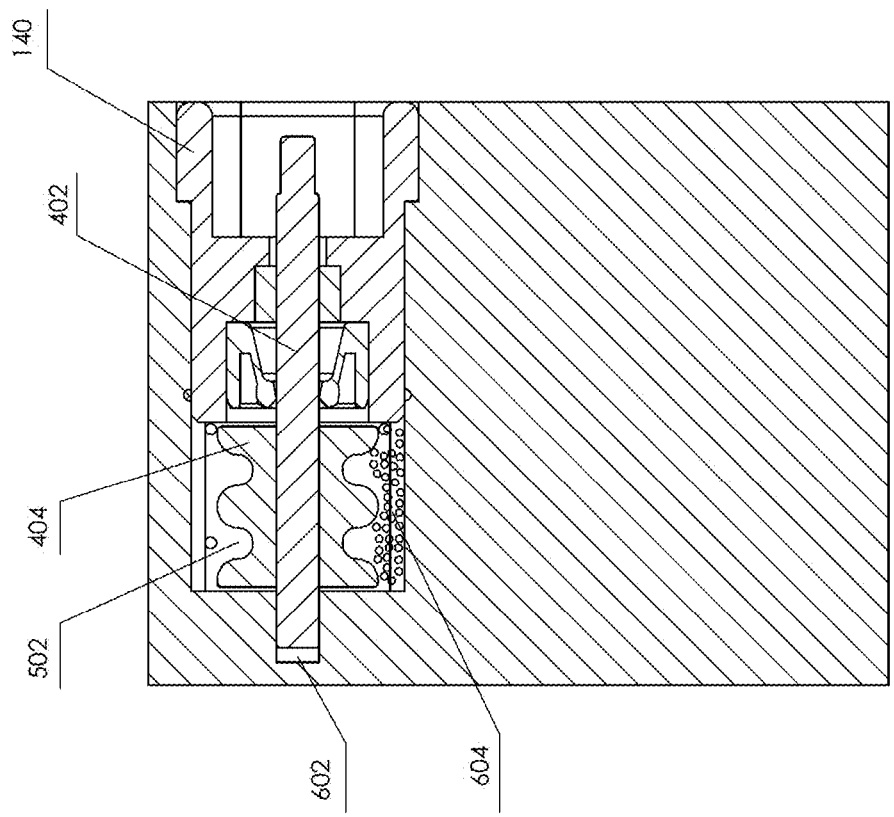
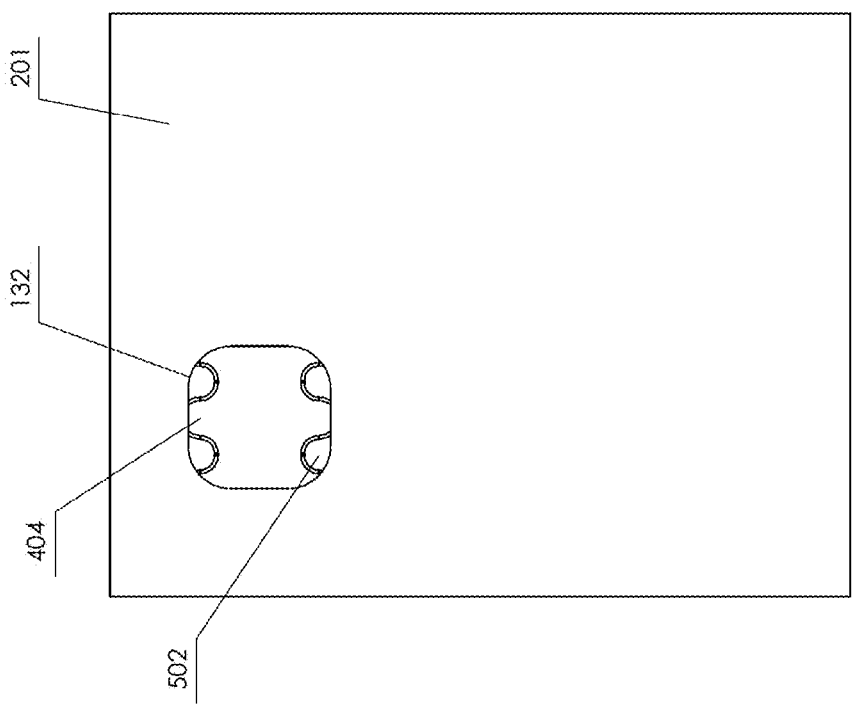
Fig.6B
Fig.6A

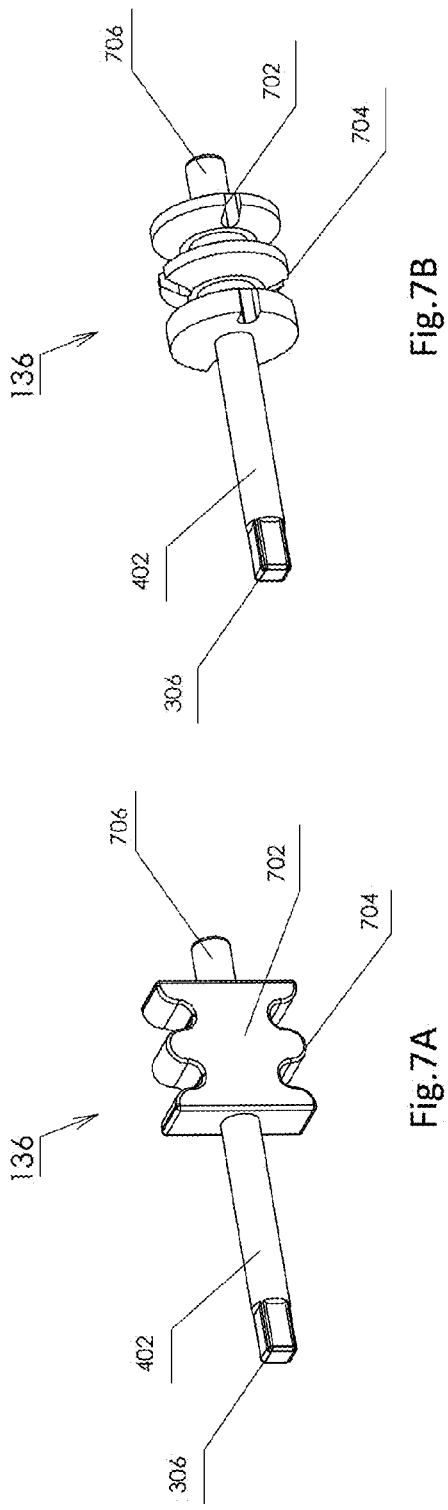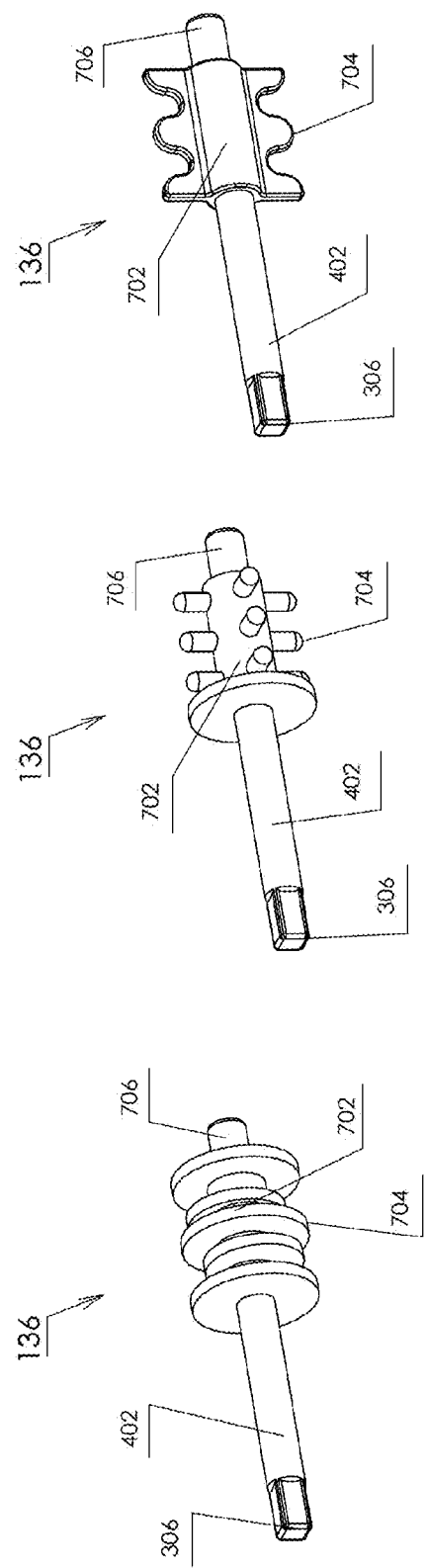

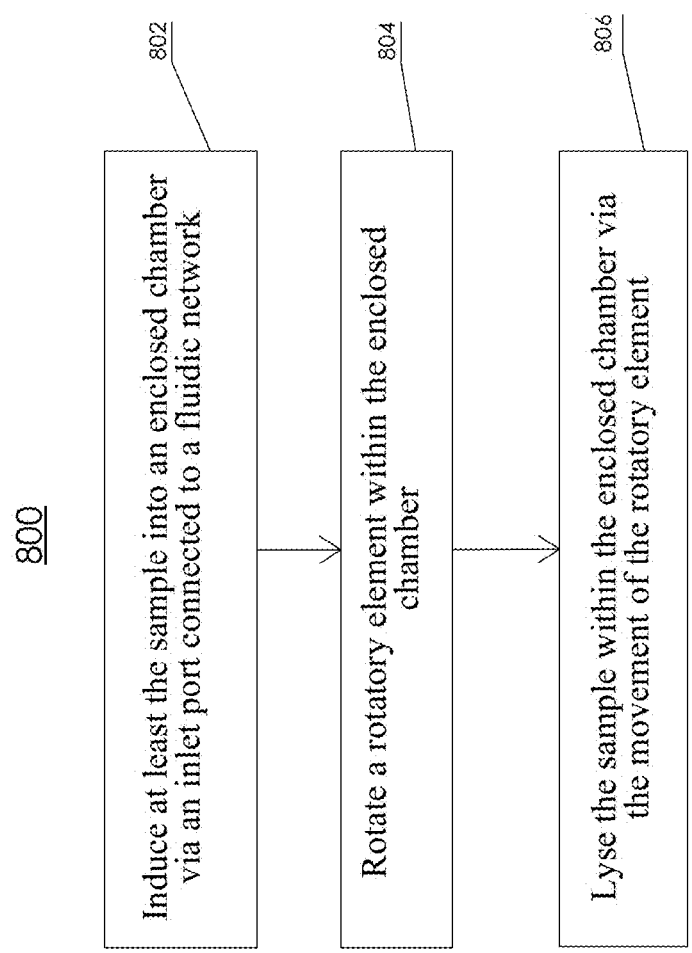

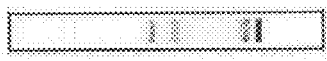
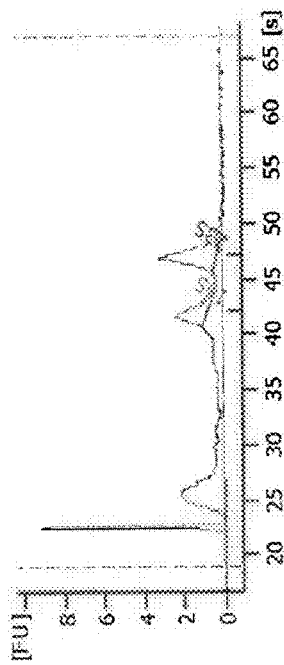
FIG. 17B
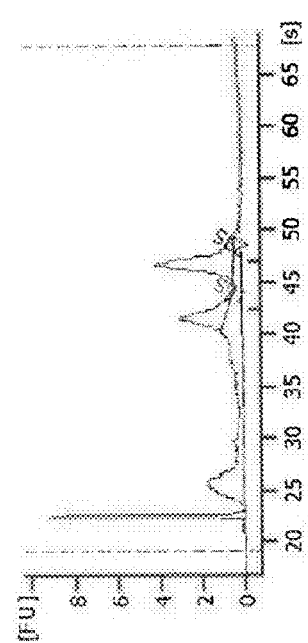
FIG. 17C

FLUIDICALLY INTEGRATED ROTARY BEAD BEATER

CROSS-REFERENCE TO RELATED APPLICATIONS

This application claims the benefit under 35 U.S.C. §119(e), to provisional application No. 61/622,858 filed on Apr. 11, 2012, the disclosure of which is incorporated by reference herein in its entirety.

BACKGROUND

1. Field

Embodiments of the present invention relate to bead beaters.

2. Background

Given the complexity of the automation of molecular testing and immunoassay techniques, there is a lack of products that provide adequate performance to be clinically usable in near patient testing settings. Typical molecular testing includes various processes involving the correct dosage of reagents, sample introduction, sample homogenization, lysis of cells to extract DNA and/or RNA, purification steps, and amplification for its subsequent detection. Even though there are central laboratory robotic platforms that automate some of these processes, for many tests requiring a short turnaround time, the central laboratory cannot provide the results in the needed time requirements.

The homogenization and/or lysis of a biological specimen is usually the initial step in a testing process such that a suitably purified analyte or analytes can be obtained for molecular testing. Generally speaking there are three main approaches to cell lysis: chemical, enzymatic and physical. These processes may be used alone or in combination, sequentially or in a single step, to achieve a more optimal process. The use of chemical and enzymatic processes can prove problematic as some chemicals used to rupture the cell wall can denature any enzymes present or generate problems in subsequent processes.

Physical methods for cell rupture include sonication, heating (usually between 90° C.-100° C.), repeated freeze-thawing, creation of rapid and large changes in pressure and mechanical methods. Mechanical methods involve the physical rupture of the cell wall through physical forces such as high-shear forces, grinding, and bombardment of the cell with small particles, often consisting of beads. Mechanical methods of disruption have a number of advantages. They often employ a one-step process, are generally very rapid, are amenable to automation, and have the ability to disrupt solid specimens, such as bone, where the analyte(s) of interests may not be made obtainable without mechanical homogenization.

BRIEF SUMMARY

Mechanical bead beater systems and methods that can be integrated with a near patient testing system are provided.

In an embodiment, a system for at least one of homogenization and lysis of a sample includes one or more walls forming an enclosed chamber having an inlet and a plurality of fluidic connections. A first fluidic network is coupled to at least one of the plurality of fluidic connections and a second fluidic network is coupled to at least one of the plurality of fluidic connections. The system further includes a rotary element within the chamber, and an actuator configured to rotate the rotary element. The first fluidic network is configured to introduce at least a sample into the chamber from at least one first reservoir. The second fluidic network is configured to expel at least the sample from the chamber to at least one second reservoir. The rotary element is rotated by the actuator about an axis extending along a length of the rotary element.

In an embodiment, a system for performing molecular testing includes a housing with one or more fluid chambers and a fluidic network, a bead beater disposed within the housing, and an actuator. The fluidic network connects at least the one or more fluid chambers to a movable central chamber. The bead beater further includes one or more walls forming an enclosed chamber with an inlet and a plurality of fluidic connections, and a rotary element within the enclosed chamber. At least a portion of the plurality of fluidic connections are coupled to the fluidic network of the housing. The rotary element is rotated by the actuator about an axis extending along a length of the rotary element.

An example method of lysing a sample is described. The method includes introducing a sample into an enclosed chamber via a fluidic connection coupled to a fluidic network that is further coupled to one or more other chambers. The method further includes rotating a rotary element within the enclosed chamber along an axis extending along a length of the rotary element. The method further includes lysing the sample within the enclosed chamber via the movement of the rotary element.

Another example method of lysing a sample is described. The method includes introducing a sample into an enclosed chamber via a fluidic connection coupled to a fluidic network that is further coupled to one or more other chambers. The method further includes rotating a rotary element within the enclosed chamber along an axis extending along a length of the rotary element. The method further includes exciting a plurality of beads within the enclosed chamber by the movement of the rotary element. The method further includes lysing the sample within the enclosed chamber via the movement of the rotary element and the plurality of beads.

An example method of homogenizing a sample is described. The method includes introducing a sample into an enclosed chamber via a fluidic connection coupled to a fluidic network that is further coupled to one or more other chambers. The method further includes rotating a rotary element within the enclosed chamber along an axis extending along a length of the rotary element. The method further includes homogenizing the sample within the enclosed chamber via the movement of the rotary element.

Another example method of homogenizing a sample is described. The method includes introducing a sample into an enclosed chamber via a fluidic connection coupled to a fluidic network that is further coupled to one or more other chambers. The method further includes rotating a rotary element within the enclosed chamber along an axis extending along a length of the rotary element. The method further includes exciting a plurality of beads within the enclosed chamber by the movement of the rotary element. The method further includes homogenizing the sample within the enclosed chamber via the movement of the rotary element and the plurality of beads.

BRIEF DESCRIPTION OF THE DRAWINGS/FIGURES

The accompanying drawings, which are incorporated herein and form a part of the specification, illustrate embodiments of the present invention and, together with the description, further serve to explain the principles of the invention and to enable a person skilled in the pertinent art to make and use the invention.

FIG. 1 is a graphical representation of a test cartridge platform, according to an embodiment.

FIGS. 2A-2B display a bead beater system, according to embodiments.

FIGS. 3A-3B display more views of a bead beater system, according to embodiments.

FIG. 4 displays an exploded view of a bead beater system, according to an embodiment.

FIG. 5 displays a view showing the inside of a bead beater system, according to an embodiment.

FIGS. 6A-6B display cross section views of a bead beater system, according to embodiments.

FIGS. 7A-7E display views of a rotary element, according to embodiments.

FIGS. 8-11 are diagrams illustrating methods performed by the bead beater system, according to embodiments.

FIGS. 17A-17C are Bioanalyzer rRNA profiles from *Bacillus subtilis*.

Figure 1:
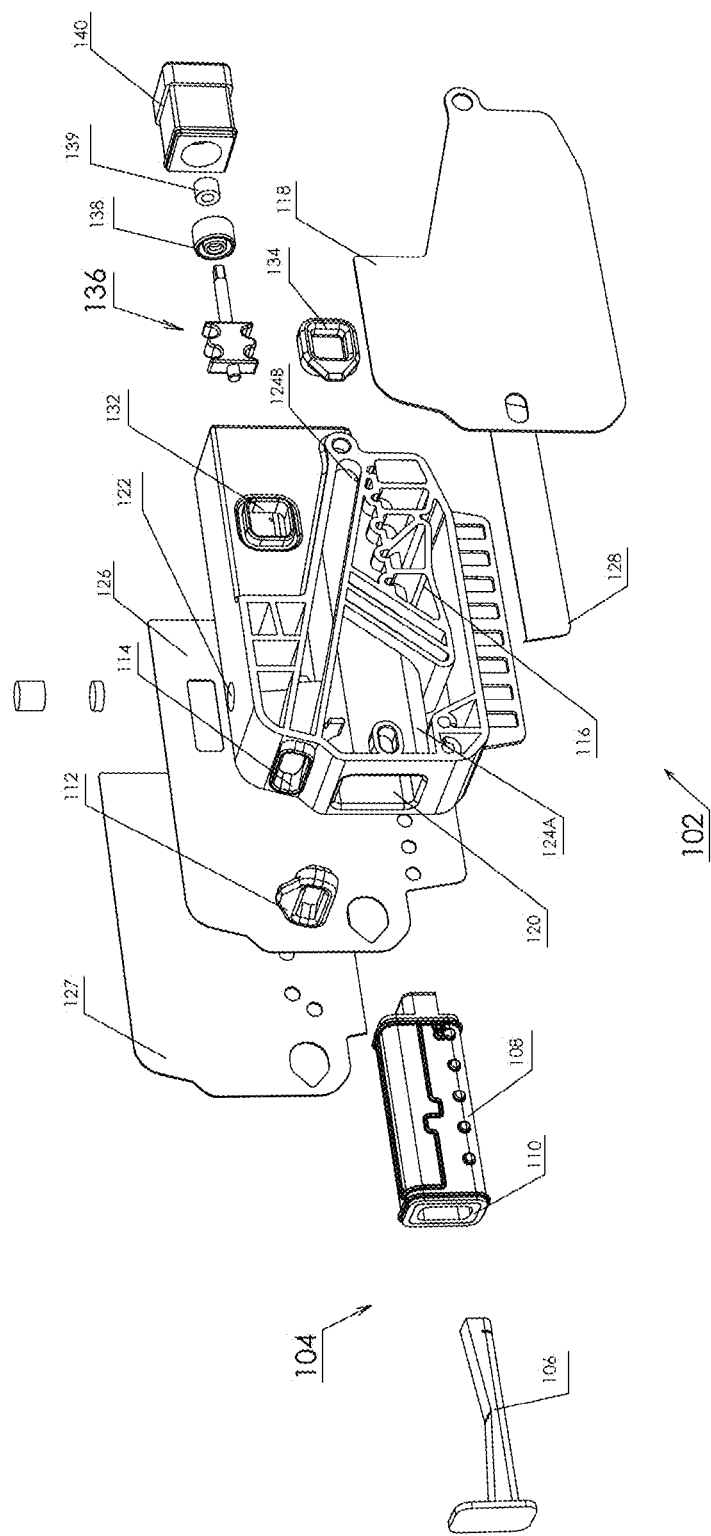

Embodiments of the present invention will be described with reference to the accompanying drawings.

DETAILED DESCRIPTION

Although specific configurations and arrangements are discussed, it should be understood that this is done for illustrative purposes only. A person skilled in the pertinent art will recognize that other configurations and arrangements can be used without departing from the spirit and scope of the present invention. It will be apparent to a person skilled in the pertinent art that this invention can also be employed in a variety of other applications.

It is noted that references in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases do not necessarily refer to the same embodiment. Further, when a particular feature, structure or characteristic is described in connection with an embodiment, it would be within the knowledge of one skilled in the art to effect such feature, structure or characteristic in connection with other embodiments whether or not explicitly described.

Embodiments described herein relate to a bead beater system for homogenization and/or lysing of a sample. The sample may be a liquid, solid, semi-solid, or a combination thereof. In one embodiment, the bead beater system is integrated with a test cartridge platform. The test cartridge platform includes a network of fluidic channels, a portion of which may couple to the integrated bead beater. The fluidic channels may provide the sample to a bead beater chamber, extract the sample from the bead beater chamber, and/or be used to pressurize the bead beater chamber.

The bead-beater system is designed to use physical disruption of samples by the rotating of, for example, a rotary element within the bead-beater chamber. This physical disruption may in turn be aided by the presence of beads (e.g., inert beads made of glass and/or other materials). In one example, the lysis and/or homogenization process is further optimized through the use of a lysis buffer within the bead beater chamber. In another example, enzymatic lysis is performed by applying heat to the sample. Heating the sample may be performed before the actual bead beating of the sample in some examples. In an embodiment, all the necessary reagents and components of the bead-beater are contained within the test cartridge platform.

In some embodiments, both the test cartridge platform and the integrated bead beater are designed to be disposable after use. Once the reagents or the sample are placed within the test cartridge, they do not again enter into contact with the external environment or with any part of an external measurement instrument. This feature is important for many laboratories and hospitals to safely dispose of the products after their use.

The bead-beater chamber itself is designed to be able to process a wide variety of specimens and to disrupt a wide variety of cell types. This is, in part, achieved by the availability of different test cartridge platforms that are specific to each particular specimen/cell type combination. In another example, variable conditions that are controlled by the analyzer, such as the speed and duration of rotation of the rotary element, allow for processing a wide variety of sample types.

Further details relating to the components of the bead beater system are described herein with references made to the figures. It should be understood that the illustrations of each physical component are not meant to be limiting and that a person having skill in the relevant art(s) given the description herein would recognize ways to re-arrange or otherwise alter any of the components without deviating from the scope or spirit of the invention.

FIG. 1 illustrates an example test cartridge system into which a bead beater can be integrated, according to an embodiment. Although reference will be made herein to the structure of the example test cartridge system, one of skill in the art will recognize that bead beater embodiments described herein may be used with any number of testing system types and configurations.

The test cartridge system includes a cartridge housing 102 and a transfer module 104. Other components may be considered as well for inclusion in the test cartridge system, such as an analyzer module or various active components such as pumps or heaters. Transfer module 104 includes an inner housing 110, a jacket 108, and a lid 106. Jacket 108 is designed to fit around inner housing 110, according to an embodiment. Lid 106 is designed to seal the end of transfer module 104 to prevent leakage. Transfer module 104 is designed to be inserted into cartridge housing 102 via chamber bay 120.

Cartridge housing 102 includes a variety of fluidic channels, chambers, and reservoirs. For example, cartridge housing 102 may include a plurality of storage chambers 116 which may contain various buffers or other reagents to be used during an assay or PCR protocol. Storage chambers 116 may be pre-filled with various liquids so that the end user will not need to fill storage chambers 116 before placing the test cartridge system into an analyzer. Cartridge housing 102 may further include one or more processing chambers 124a-b connected to fluidic channels along a side of cartridge housing 102. Processing chambers 124a-b may be used for a variety of processing and/or waste applications. In one example, chamber 124*a* is a waste chamber, and chamber 124*b* is a chamber dimensioned to receive the length of a swab having a sample thereon.

Samples are introduced into cartridge housing 102 via sample port 114, according to an embodiment. A user may place a swab completely within sample port 114 and its corresponding chamber 124*b*, and subsequently seal the port with a port lid 112. In another example, sample port 114 receives solid, semi-solid, or liquid samples. In an embodiment, cartridge housing 102 includes more than one inlet to introduce samples.

The various chambers and channels around cartridge housing 102 may be sealed via the use of covers 118, 126, 127, and 128. The covers may be films capable of sealing the fluid within cartridge housing 102. In another example, the covers may be plastic panels. In an example, one or more of the covers are transparent. Additionally, one or more of the covers may be thermally controlled for heating portions of housing 102.

The integrated test cartridge system allows a user to place a sample into, for example, sample port 114, then place the test cartridge system into an analyzer. In embodiments, the reaction steps to be performed including, for example, purification, lysing, mixing, binding, labeling and/or detecting can all be performed within the test cartridge system via interaction with the analyzer without any need for the end user to intervene. Additionally, since all of the liquids remain sealed within the test cartridge system, after the test is completed, the test cartridge system may be removed from the analyzer and safely disposed of without contamination of the analyzer.

The test cartridge system may further include fluidic channels which lead to an inner processing chamber having an opening 132. In an embodiment, the inner processing chamber is an integrated bead beater chamber disposed within cartridge housing 102. Although the chamber itself is hidden from view in FIG. 1, various other components of the system are shown in the exploded view. For example, the bead beater system includes a processing lid 134 that fits over opening 132. Within the chamber itself, a rotary element 136 is disposed, according to an embodiment. In an embodiment, rotary element 136 couples to an actuator (not shown) via seal 138 and bushing 139. Seal 138 and bushing 139 may be held in place by a support 140. In one example, seal 138 is a lip seal. Other types of sealing components may be utilized. Support 140 may also fit into the end of the inner processing chamber and seal it from any leaks. Each of the components of the bead beater system will be explained in more detail herein.

Figure 2B:
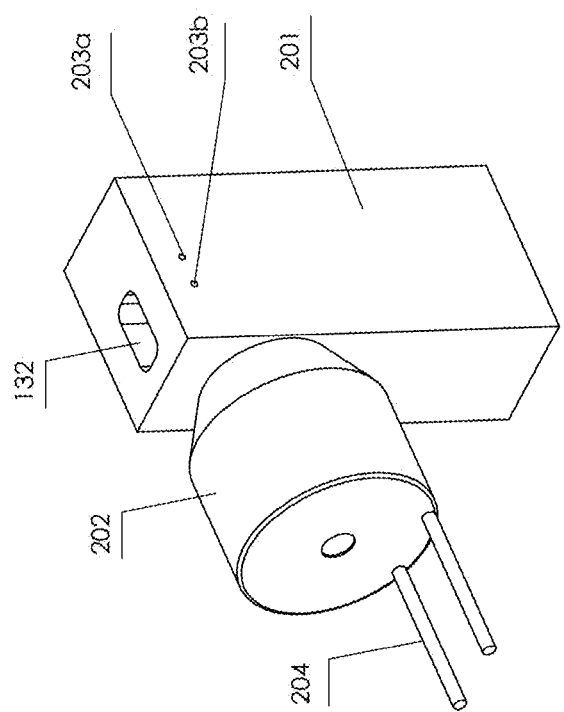
Figure 2A:
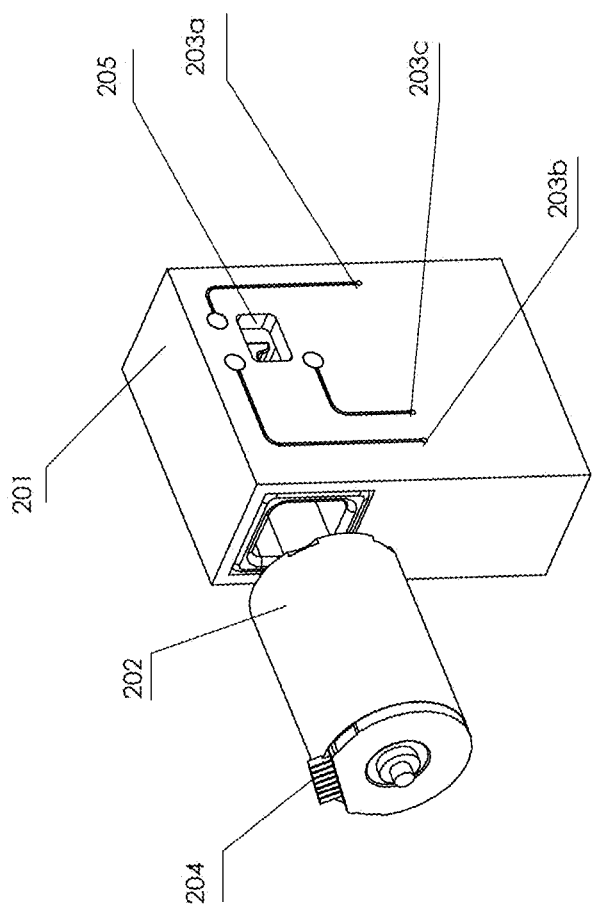

FIGS. 2A and 2B illustrate example embodiments of a rotary bead beater system. Similar features in both embodiments are given the same numerical label. The description of each embodiment is set forth to describe features that may be present on or within the bead beater system, but should not be limiting as to the placement or dimensional properties of the features.

FIGS. 2A and 2B provide a perspective view of a bead beater 201 which can be integrated into the test cartridge system, according to embodiments. The outer view of bead beater 201 illustrated in FIG. 2B displays processing inlet 132 at a top surface of bead beater 201, according to an embodiment. In the beat beater embodiment illustrated in FIG. 2A, the processing inlet is on a side of bead beater 201 facing away from the page, and is thus not shown. Processing inlet 132 is configured to accept any type of sample, including liquid, solid, semi-solid, or any combination thereof. Processing inlet 132 leads into an enclosed chamber where the bead beating process takes place. In another example, samples entering processing inlet 132 are lead to a first chamber, and then transferred from the first chamber into a second chamber where the bead beating process takes place.

On one side of bead beater 201, fluid inlets are provided to couple with a fluidic network. The bead beater embodiment of FIG. 2A has three fluid inlets 203*a-c*, while the bead beater embodiment of FIG. 2B has two fluid inlets 203*a* and 203*b*. For example, fluid inlets 203*a-c* may couple to any of storage chambers 116 of cartridge housing 102. In an embodiment, fluid inlets 203*a-c* lead into the chamber where the bead beading takes place. As such, fluid inlets 203*a-c* may be used for introducing any liquid into the bead beating chamber, extracting any liquid from the bead beating chamber, or for applying a pressure differential in the bead beating chamber, or any combination thereof. It should be understood that any number of fluidic connections may exist leading into the bead beating chamber. Furthermore, any of the plurality of fluidic connections may lead to one or more chambers of cartridge housing 102. In an embodiment, a first fluidic network is coupled to the fluid inlets and introduces at least a sample to the chamber from a first reservoir, while a second fluidic network is coupled to the fluidic connections and is used to expel at least the sample from the chamber to a second reservoir. In an embodiment, the fluidic networks, the bead beater, and the reservoirs form an enclosed system.

External to bead beater 201, an actuator system 202 is attached to rotary element 136 (not shown) disposed within the bead beater chamber, according to an embodiment. In one example, actuator system 202 is a rotary actuator. Actuator system 202 may receive various signals via coupling 204. For example, the signals may include power or control signals. Coupling 204 may represent wires, RF signals, or optical signals. Actuator system 202 may rotate rotary element 136 at any speed within the capabilities of actuator system 202. In one example, actuator system 202 rotates rotary element 136 at speeds ranging from 50 RPM to 30,000 RPM.

The embodiment of bead beater 201 illustrated in FIG. 2A also includes a cavity 205 disposed on a side wall of bead beater 201. Cavity 205 may be covered by a thermally conductive material, such as, for example, an aluminum foil. By heating the thermally conductive material, the contents within the inner processing chamber of bead beater 201 may be heated via cavity 205. It should be understood that the placement of cavity 205 is not limited to the side of bead beater 201. The cavity may also be disposed on top of bead beater 201 or on a back surface of bead beater 201. In another example, one or more of the walls of the inner processing chamber may be a thermally controlled surface to heat the contents of the inner processing chamber without requiring a cavity. One or more of the walls of the inner processing chamber may be manufactured from metals having a high thermal conductivity such as aluminum, copper, etc. Introducing heat into the inner processing chamber may allow for enzymatic lysis of a sample to occur. In one example, enzymatic lysis may be performed using an applied heat to a sample before the actual bead beating of the sample commences.

Figure 3A:
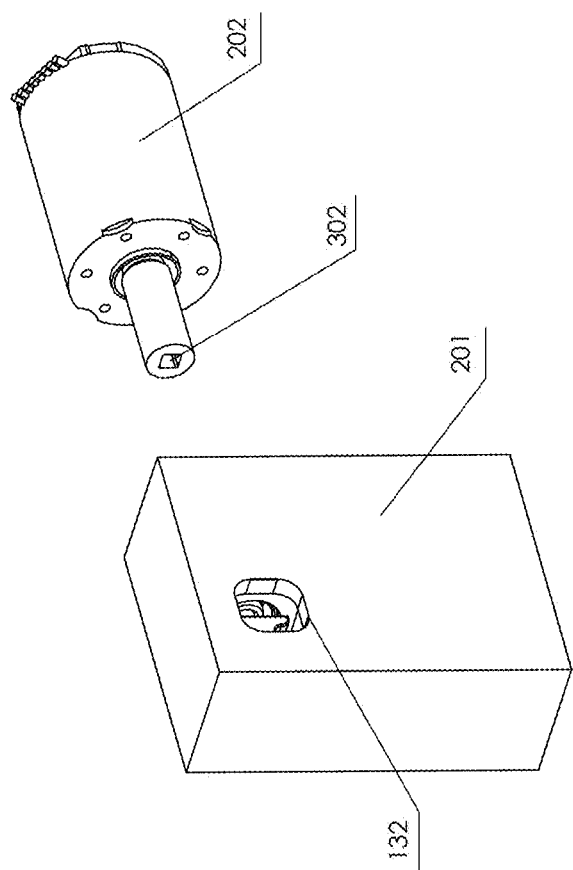

FIG. 3A illustrates another view of bead beater 201 with actuator 202 detached from the main body of bead beater 201. A coupling element 302 is provided to attach actuator 202 to rotary element 136 (not shown) within the bead beater chamber. Coupling element 302 may be, for example, a shaft, screw, or a recess for receiving another element. Actuator 202 is configured to be manually or automatically detachable from rotary element 136 within the bead beater chamber with little effort required by the user. Coupling element 302 may be suitably shaped to fit within a receiving portion of rotary element 136, or may itself receive a portion of rotary element 136. According to an embodiment, rotation of coupling element 302 causes rotation of rotary element 136.

Figure 3B:
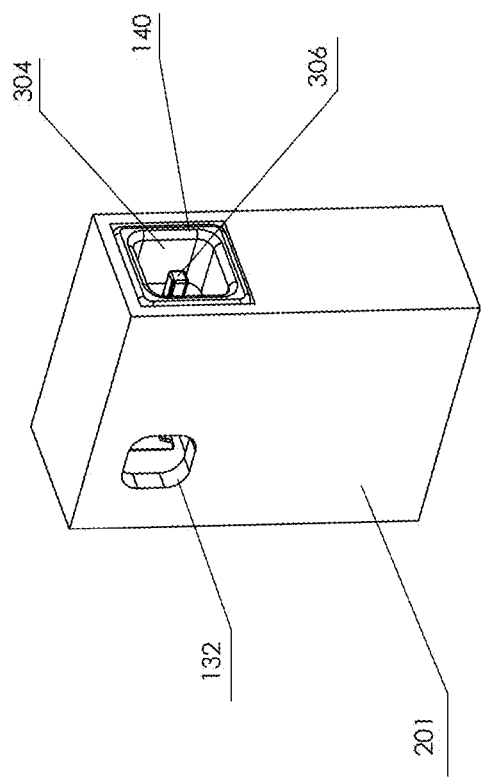

FIG. 3B illustrates another view of bead beater 201, according to an embodiment. FIG. 3B illustrates another angle view of bead beater 201 as shown in FIG. 2A with actuator 202 removed. Support 140 is shown plugging into a hole on the side of bead beater 201, according to an embodiment. An outside portion of support 140 includes a recess 304. Within recess 304, part of rotary element 136 extends out from the enclosed chamber, according to an embodiment. This section of rotary element 136 includes a structure 306. Structure 306 may be designed to snugly fit into coupling element 302 from actuator 202. In an example, rotation of coupling element 302 by actuator 202 causes substantially the same rotation to occur with structure 306 on the end of rotary element 136.

Figure 4:
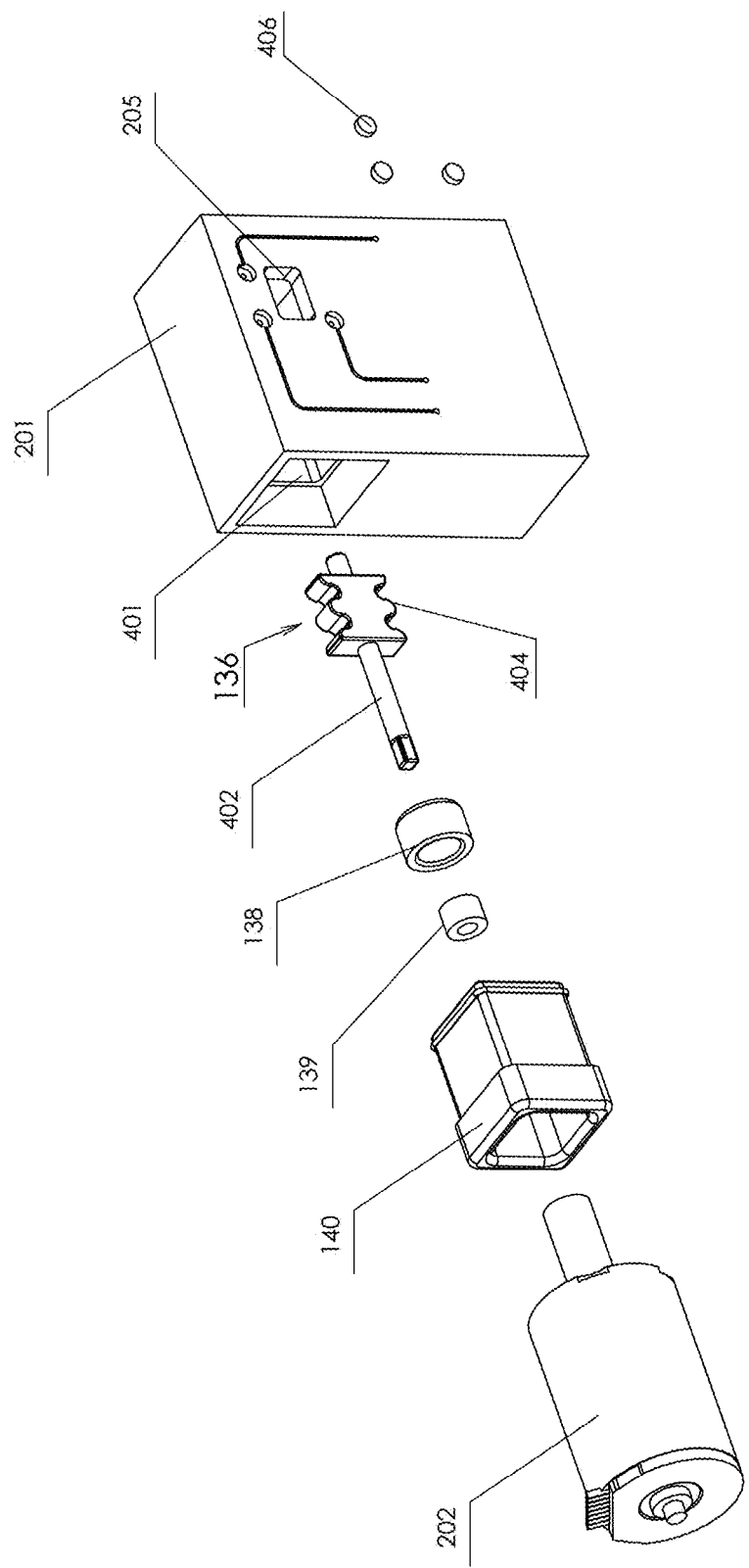

FIG. 4 illustrates an exploded view of various components of rotary element 136 and actuator 202, according to an embodiment. Opening 401 of bead beater 201 accepts support 140 which facilitates the connection of actuator 202 with rotary element 136, according to an embodiment. Additional elements may be included as well for connecting rotary element 136 to actuator 202, such as, for example, seal 138 and bushing 139. These elements may also provide a barrier to keep samples within the bead beater chamber from leaking out from the area around where rotary element 136 extends out from the chamber.

Shaft 402 connects structure 306 on the end of rotary element 136 with a rotating body 404, according to an embodiment. Rotating body 404 may take on various shapes and sizes. The length of shaft 402 may be adjustable for various sizes of bead beater chambers. It should be noted that, in some embodiments, all of the components shown except for actuator 202 are intended to be disposable after a single use, or series of uses during a single test, of bead beater 201.

Also illustrated on a side of beat beater 201 are a plurality of frits 406. Each frit 406 may include various materials designed to filter or trap various particle sizes. In one example, frit 406 is a plastic material having a thin mesh with selectable pore sizes that may range anywhere between 5 microns to 500 microns. In one embodiment, frit 406 has a pore size of around 20 microns. Fluid extracted from the bead beater chamber may pass through at least one of fits 406 in order to be filtered.

Figure 5:
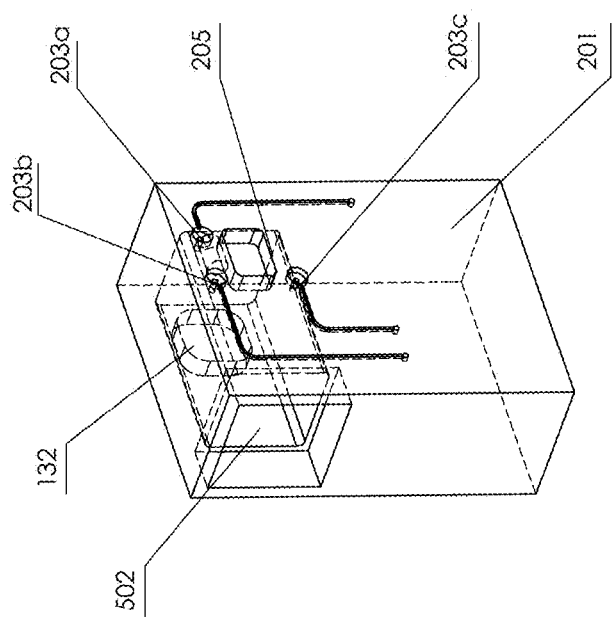

FIG. 5 illustrates a view inside the bead beater chamber of bead beater 201. An enclosed chamber 502 provides the area where homogenization and/or lysing of samples takes place. In an embodiment, enclosed chamber 502 is substantially cylindrical in shape. The cylindrical shape provides an efficient fluid motion around the rotary element as it rotates. Enclosed chamber 502 may also have a rectangular cross section. Other shapes of enclosed chamber 502 may be considered as well for enhancing the agitation of, for example, a plurality of beads disposed within enclosed chamber 502. The use of a plurality of beads to improve the homogenization and/or lysis process is described in more detail with regards to FIG. 6B.

Various fluidic connections to enclosed chamber 502 are included, according to an embodiment. Fluid inlets 203*a-c* are shown along a side as described previously. In one example, a sample and/or other liquids may be introduced into enclosed chamber 502 via fluid inlet 203*a* or 203*b*. In another example, the resultant mixture following either lysing or homogenization may be expelled from enclosed chamber 502 via fluid inlet 203*c*. The various fluidic connections may be placed anywhere around enclosed chamber 502 and at any angle. Processing inlet 132 and heating cavity 205 are illustrated as well on the sides of enclosed chamber 502. A thermally controlled surface may seal heating cavity 205 and heat the contents of enclosed chamber 502. In one example, heating the contents of enclosed chamber 502 causes enzymatic lysing to occur. In another example, shaft 402 may be rotated to agitate the sample and homogenate the temperature inside of enclosed chamber 502 during the heating process.

FIG. 6A illustrates a side view of bead beater 201 looking into processing inlet 132 with the cover removed, according to an embodiment. In one example, rotating body 404 is observed as being substantially centered within enclosed chamber 502.

FIG. 6B illustrates a cross section view of the interior of enclosed chamber 502 including support 140, according to an embodiment. Shaft 402 extends through support 140 and connects to rotating body 404 within enclosed chamber 502. One end of shaft 402 is configured to fit into a notch 602 of enclosed chamber 402, according to an embodiment. Notch 602 may be used to stabilize the position of shaft 402 within enclosed chamber 502, while still allowing for rotation of rotating body 404. Enclosed chamber 502 may also include a plurality of beads 604. The beads may be included to aid in the homogenization and/or lysing process of a sample within enclosed chamber 502. The rotation of rotating body 404 excites plurality of beads 604 into movement as well. Individual beads in plurality of beads 604 may range in size from one micron in diameter up to 3000 microns in diameter. Additionally, plurality of beads 604 may be manufactured from various inert materials, including plastics, glass, ceramics, and silica.

FIGS. 7A-7E illustrate various embodiments of rotary element 136. These embodiments are exemplary, and it should be understood that other designs could also be contemplated by one having ordinary skill in the art given the description herein. Rotary element 136 in each embodiment includes shaft 402 with structure 306 at one end as described previously. Various designs are illustrated for body 702 and features 704. Body 702 may be any material suitably hard enough to perform homogenization of tough sample types, such as bone and tissue. Additionally, body 702 may be a material that is biocompatible. Features 704 are provided to give a patterned shape to body 702. The rotation of features 704 within enclosed chamber 502 causes rapid movement of the sample and any other material around the chamber. In another example, the rotation of features 704 causes excitation and movement of plurality of beads 604. Each illustrated design also includes a peg 706 at one end of rotatory element 136, according to some embodiments. Peg 706 may be configured to fit within notch 602 of enclosed chamber 502. It should be understood that peg 706 is not a required element of rotary element 136, but may be used to enhance stability within enclosed chamber 502.

FIGS. 8-11 describe example methods to be employed for homogenizing or lysing a sample with or without beads, according to embodiments. It should be understood that methods 800, 900, 1000, and 1100 describe example operation sequences that can be performed with bead beater 201, and should not be considered limiting. Any of methods 800, 900, 1000, and 1100 may also include a step of heating the contents within bead beater 201 to perform an enzymatic lysis. In one example, the enzymatic lysis is performed before the bead beating occurs.

FIG. 8 displays a flowchart of an example method 800 for lysing a sample using bead beater 201. The objective of cell lysis is to release cellular contents which are required for analysis. Examples of cellular contents include, but are not limited to, DNA, RNA, polypeptides, enzymes, prions, proteins, antibodies, antigens, allergens, and virons.

At block 802, at least the sample is introduced into an enclosed chamber via an inlet port connected to a fluidic network. The sample may be introduced, for example, through fluid inlets 203a-c.

At block 804, a rotary element is rotated within the enclosed chamber. The rotary element is configured to be rotated along an axis extending along a length of the rotary element by an external actuator.

At block 806, the sample is lysed within the enclosed chamber via the movement of the rotary element. The lysate may be transferred from the enclosed chamber to a second chamber via one of fluid inlets 203a-c.

Figure 9:
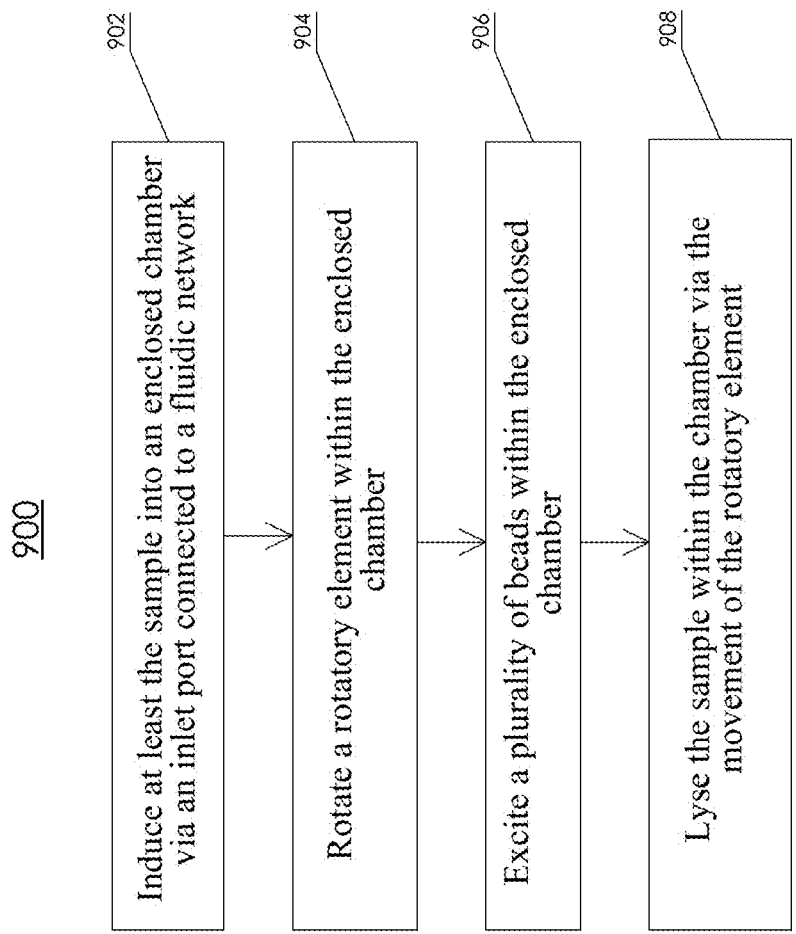

FIG. 9 displays a flowchart of an example method 800 for lysing a sample using bead beater 201 containing a plurality of heads. The objective of cell lysis is to release cellular contents which are required for analysis. Examples of cellular contents include, but are not limited to, DNA, RNA, polypeptides, enzymes, prions, proteins, antibodies, antigens, allergens, and virons. The included beads act to speed up the process of tearing the cell walk to release the cellular contents.

At block 902, at least the sample is introduced into an enclosed chamber via an inlet port connected to a fluidic network. The sample may be introduced, for example, through fluid inlets 203a-c.

At block 904, a rotary element is rotated within the enclosed chamber. The rotary element is configured to be rotated along an axis extending along a length of the rotary element by an external actuator.

At block 906, a plurality of beads within the chamber are excited by the movement of the rotary element. The beads may vary in shape, size and/or material as described previously. The added movement of the beads within the chamber provide further beating of the cells and lead to a more efficient lysing process.

At block 908, the sample is lysed within the enclosed chamber via the movement of the rotary element and the plurality of beads. The lysate may be transferred from the enclosed chamber to a second chamber via one of fluid inlets 203a-c.

Figure 10:
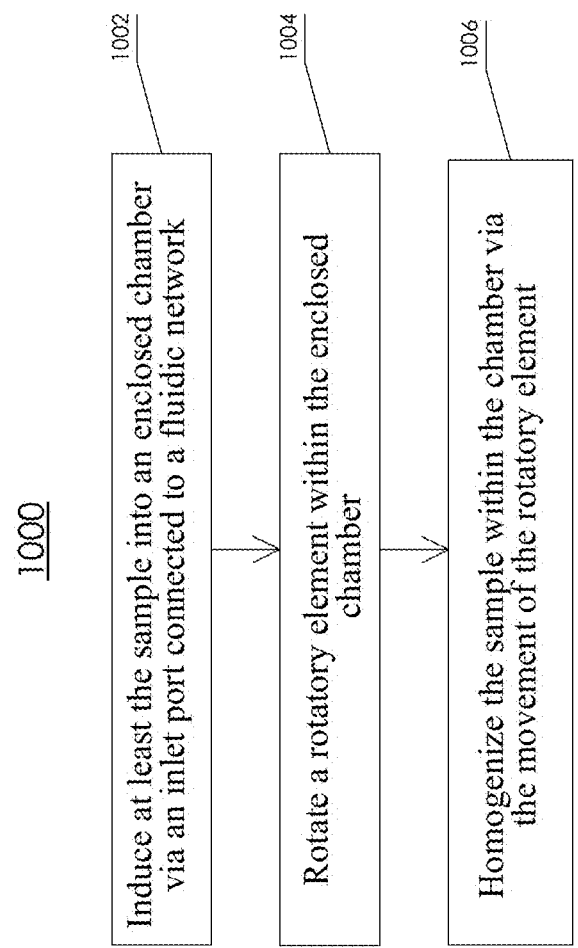

FIG. 10 displays a flowchart of an example method 1000 for homogenizing a sample using bead beater 201.

At block 1002, at least the sample is introduced into an enclosed chamber via an inlet port connected to a fluidic network. The sample may be introduced, for example, through fluid inlets 203a-c or through any other suitable port. In an embodiment, a solid, semi-solid, or liquid sample may be provided for homogenization. For example, samples with a high viscosity (e.g. sputum, tissue, bone) are well suited for homogenization to break down complex matrices that hold the cellular components of the sample together.

At block 1004, a rotary element is rotated within the enclosed chamber. The rotary element is configured to be rotated along an axis extending along a length of the rotary element by an external actuator.

At block 1006, the sample is homogenized within the enclosed chamber via the movement of the rotary element. The homogenized sample may be lysed using bead beater 201 or transferred to another chamber for further processing.

Figure 11:
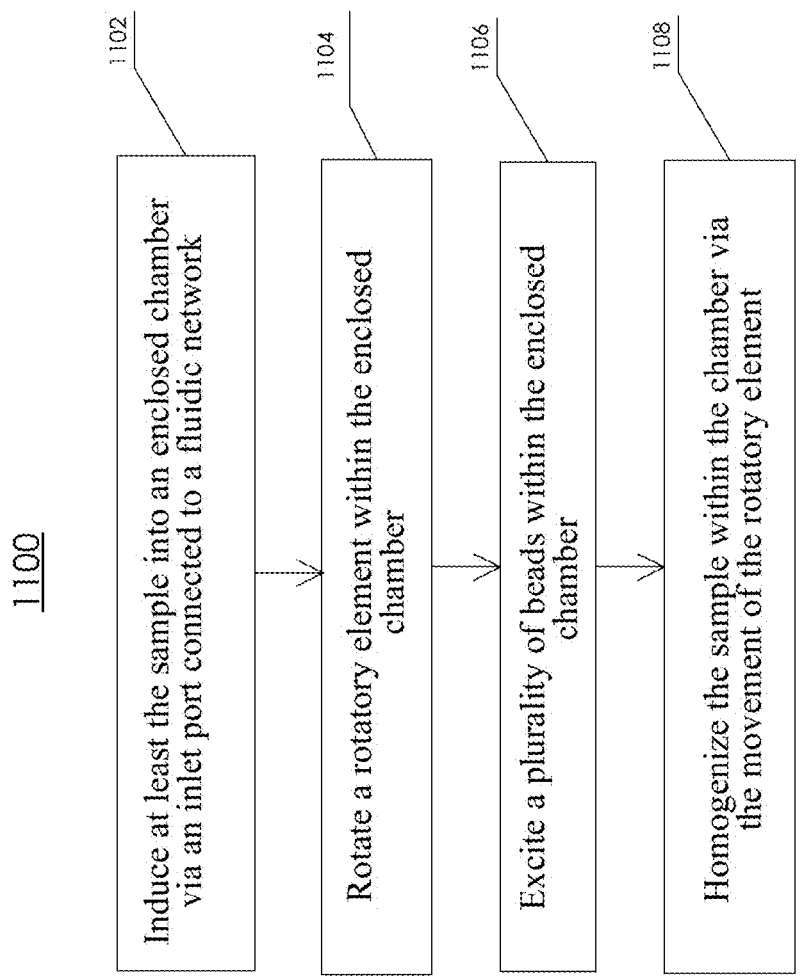

FIG. 11 displays a flowchart of an example method 1000 for homogenizing a sample using bead beater 201 containing a plurality of beads.

At block 1102, at least the sample is introduced into an enclosed chamber via an inlet port connected to a fluidic network. The sample may be introduced, for example, through fluid inlets 203a-c or through any other suitable port. In an embodiment, a solid, semi-solid, or liquid sample may be provided for homogenization. For example, samples with a high viscosity (e.g. sputum, tissue, bone) are well suited for homogenization to break down complex matrices that hold the cellular components of the sample together.

At block 1104, a rotary element is rotated within the enclosed chamber. The rotary element is configured to be rotated along an axis extending along a length of the rotary element by an external actuator.

At block 1106, a plurality of beads within the chamber are excited by the movement of the rotary element. The beads may vary in shape, size and/or material as described previously. The added movement of the beads within the chamber provide further beating of the sample and a more efficient homogenization process.

At block 1108, the sample is homogenized within the enclosed chamber via the movement of the rotary element and the plurality of beads. The homogenized sample may be lysed using bead beater 201 or transferred to another chamber for further processing.

EXAMPLES

Example protocols performed using embodiments of bead beater 201 are now discussed. Such protocols are examples only, and not limiting on embodiments of the present invention. For the example protocols, the extracted DNA and RNA from various samples were analyzed and compared to controls to determine the effectiveness of the bead beater. It should be understood that the steps recited here provide just a few possible examples for using the system.

Example 1

DNA Extraction from *Bacillus subtilis* Endospores

*Bacillus subtilis*, known also as the hay *bacillus* or grass *bacillus*, is a Gram-positive, catalase-positive bacterium. A member of the genus *Bacillus, B. subtilis* is rod-shaped, and has the ability to form a tough, protective endospore, allowing the organism to tolerate extreme environmental conditions. Endospores of various *Bacillus* species are formed in sporulation, a process that is generally induced by reduced levels of nutrients in the environment. Endospores contain an outer spore cortex that is extremely resistant to harsh physical and chemical treatments making it challenging to identify a spore lysis method that can be completed in a few minutes.

An example protocol for lysing the cells of *Bacillus subtilis* is adapted from W. Nicholson and P. Setlow, *Molecular Biological Methods for Bacillus*, New York, John Wiley, pp. 391-450, 1990. In this example protocol, a 100 mL culture of *Bacillus subtilis* subsp. *spizizenii* (ATCC 6633) grown in sporulation medium (SM) is vortexed, then separated in two volumes of 50 mL. After centrifugation at 3750 g for 15 minutes, the pellets are washed three to five times with 50 mL sterile cold distilled water, each wash being centrifuged at 3750 g for 15 minutes. The final pellets are re-suspended in 50 mL of sterile cold distilled water. Spore suspensions are treated with DNase to remove external residual DNA, quantified and diluted to a final concentration of $5 \times 10^9$ endospores/mL Serial 10-fold-dilutions are prepared ($5 \times 10^9$, $5 \times 10^7$, $5 \times 10^5$, $5 \times 10^3$ and 50 endospores/mL) in Tris-EDTA buffer to be used as a starting material in the fluidically integrated rotatory bead beater.

First, 400 mg of sterile, acid washed glass beads with a diameter of 150-212 µm (SIGMA G1145-100G) are introduced into the bead beater chamber. Second, a 200 µL endospores dilution is re-suspended in 200 µL Tris-EDTA buffer 1× and is transferred to the bead beater chamber via the processing inlet. The bead beater is operated with a rotary speed of 10,000 RPM for about 2 minutes. Bacterial nucleic acids are released when spores are disrupted by the mechanical action of the bead beater. Nucleic acid extractions remain stable for several months when stored frozen at −80° C. or −20° C. and may be frozen and thawed several times without any significant loss in PCR analytical sensitivity.

Amplification and detection of DNA from *Bacillus subtilis* endospores is performed on the StepOnePlus™ Real-Time PCR System from Applied Biosystems with the PremixEx-Taq (Probe qPCR) from Takara (cat. RR390A), according to the manufacturer's instructions. 1.5 µL of prepared lysate is added directly to a qPCR reaction consisting of 1× Premix Ex Taq (contains TaKaRa Ex Taq HS, dNTP Mixture, $Mg^{2+}$, and Tli RNaseH), 1×ROX reference dye, 0.50 µM of each SpoA *Bacillus subtilis*-specific primer, 0.20 µM of SpoOA TaqMan® probe and 0.2 mg/mL BSA; in a final volume of 15 µL. In parallel, spores without processing were tested as untreated controls (at the same concentrations). 1.5 µL of distilled water is also added to a qPCR reaction as a negative control. The optimal cycling conditions for maximum sensitivity and specificity are 10 seconds at 95° C. for initial denaturation, then fifty cycles of two steps consisting of 1 second at 95° C. and 10 seconds at 60° C. Amplification is monitored during each elongation cycle by measuring the level of fluorescence. DNA concentrations are also calculated by interpolating Ct values (number of PCR cycles needed to produce a positive signal) in a calibration curve. Table 1 below provides the SpoOA *Bacillus subtilis*-specific primers and probe sequence used in the TaqMan® qPCR reaction.

TABLE 1

| Primer | Sequence (5'->3') | Length (bp) | Product size (bp) |
|---|---|---|---|
| SpoOA F | ccatcatcgcaaagcagtatt | 21 | 70 |
| SpoOA R | tgggacgccgattcatg | 18 | |
| SpoOA Probe | ctcgacgcgagcatcacaagcatt | 24 | |

Figure 12:
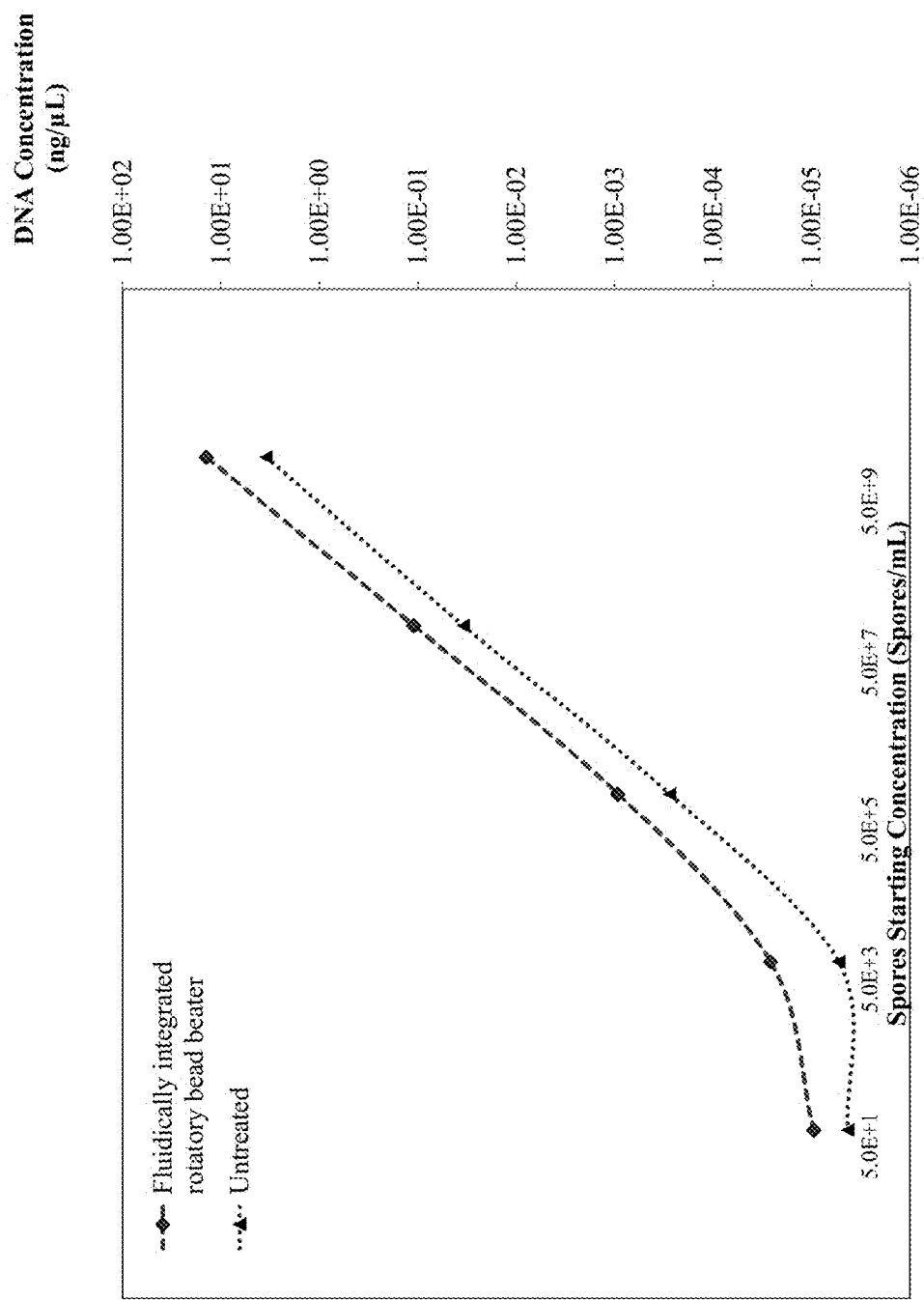
FIG. 12 is a graph of measured DNA concentration from *Bacillus subtilis* spores.

FIG. 12 provides a graph of the results from the DNA extraction protocol for *Bacillus subtilis*. The results are shown based on the extracted DNA concentration compared to the starting concentration of *Bacillus subtilis* spores. Results are a mean of 15 replicates at each concentration. As observed, the endospores lysed with the fluidically integrated rotary bead beater yielded higher DNA concentrations than the untreated endospores for every starting concentration of *Bacillus subtilis* spores.

Example 2

DNA Extraction from *Bacillus subtilis* Vegetative Cells

In this example, the bead beater is first loaded with 400 mg of sterile, acid washed glass beads with a diameter of 150-212 µm (SIGMA G1145-100G). A volume of 3 mL of broth culture of *Bacillus subtilis* subsp. *spizizenii* (ATCC 6633) vegetative cells in mid-log phase of growth (O.D550=0.60-0.70) is centrifuged and the pellet is re-suspended in Tris-EDTA buffer to obtain a final *Bacillus subtilis* concentration at 5×108 CFU/mL. Serial 10-fold-dilutions are prepared ($5 \times 10^8$, $5 \times 10^6$, $5 \times 10^4$, $5 \times 10^2$ and 5 CFU/mL) in Tris-EDTA buffer. 200 µL of vegetative cells dilution is re-suspended in 200 µL Tris-EDTA buffer 1× and the final mixture is transferred to the bead beater device by the processing inlet. The bead beater is operated with a rotary speed of 10,000 RPM for about 2 minutes.

Amplification and detection of spiked DNA from *Bacillus subtilis* vegetative cells is performed on the StepOnePlus™ Real-Time PCR System from Applied Biosystems with the PremixExTaq (Probe qPCR) from Takara (cat. RR390A), according to the manufacturer's instructions. 1.5 µL of prepared lysate is added directly to a qPCR reaction consisting of 1× Premix Ex Taq (contains TaKaRa Ex Taq HS, dNTP Mixture, Mg2+, and Tli RNaseH), 1×ROX reference dye, 0.50 µM of each SpoA *Bacillus subtilis*-specific primer, 0.20 µM of SpoOA TaqMan® probe (See table 1 of Example 1) and 0.2 mg/mL BSA; in a final volume of 15 µL. In parallel, vegetative cells without processing were tested as untreated controls (at the same concentrations). 1.5 µL of distilled water is added also to a qPCR reaction as a negative control. The optimal cycling conditions for maximum sensitivity and specificity are 10 seconds at 95° C. for initial denaturation, then fifty cycles of two steps consisting of 1 second at 95° C. and 10 seconds at 60° C. Amplification is monitored during each elongation cycle by measuring the level of fluorescence. DNA concentrations are also calculated by interpolating Ct values in a calibration curve.

Figure 13:
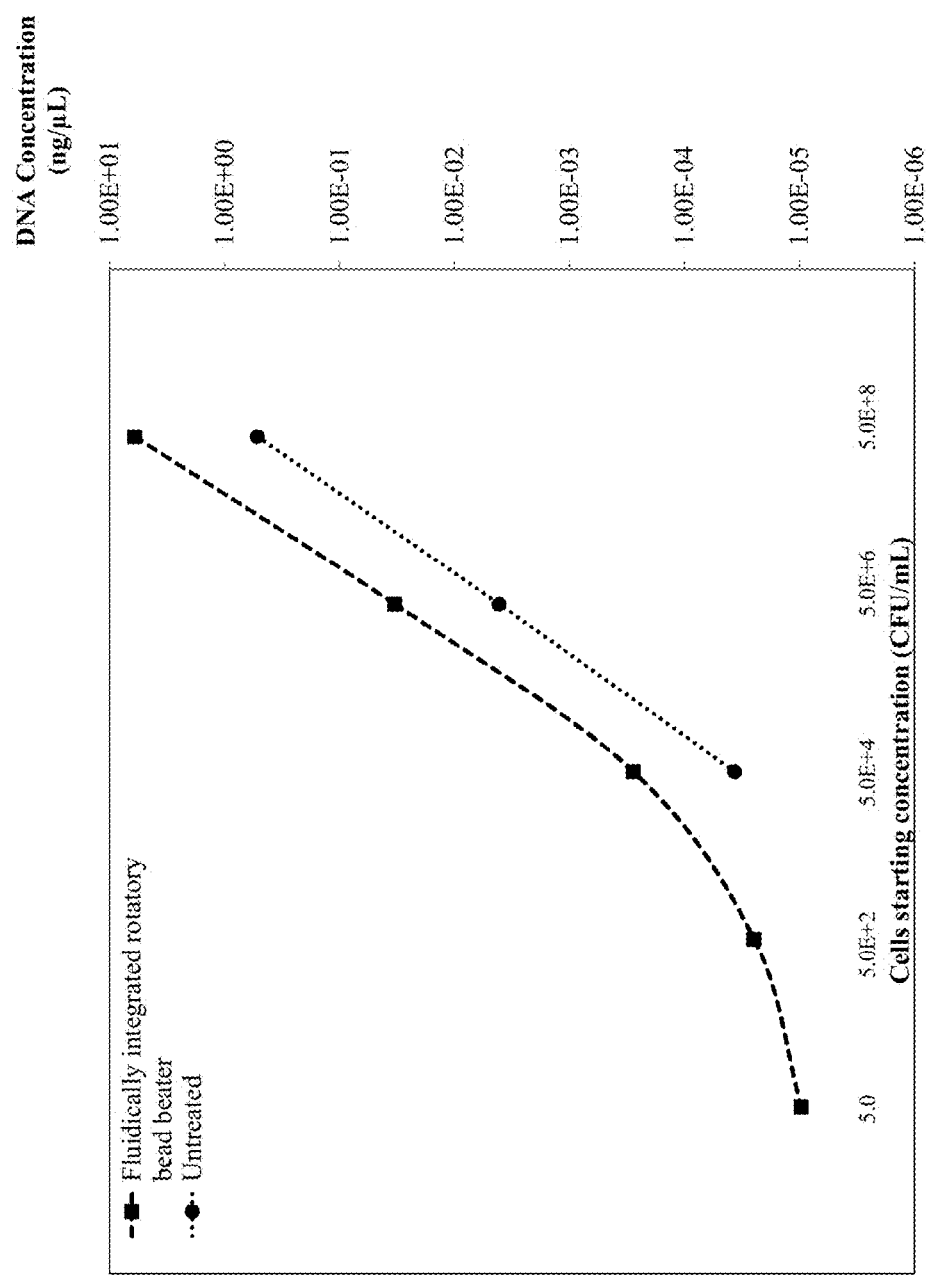
FIG. 13 is a graph measured DNA concentration from *Bacillus subtilis* vegetative cells.

FIG. 13 provides a graph of the results from the DNA extraction protocol for *Bacillus subtilis* vegetative cells. The results are shown based on the extracted DNA concentration compared to the starting concentration of cells. Results are a mean of 15 replicates at each concentration. The detection of the lysate from *B. subtilis* vegetative cells with the fluidically integrated rotatory bead beater was approximately between 50 and 500 CFU/mL (10-100 CFU per reaction). No amplification signal was observed in the untreated *B. subtilis* vegetative cells up to a $5.0 \times 10^4$ CFU/mL concentration.

Example 3

DNA Recovery Comparison for *Bacillus subtilis* Vegetative Cells

In this example, a DNA control is extracted from *B. subtilis* subsp. *spizizenii* (ATCC 6633) vegetative cells using a Norgen RNA/DNA/Protein Purification Kit. For each sample, 1.6 ng DNA are spiked in 800 µL of a buffered solution which also includes a chelating agent (Tris-EDTA buffer 1×, prepared from SIGMA Tris-EDTA buffer 100× concentrate.)

In parallel, a lysis protocol is performed on the *Bacillus subtilis* vegetative cells prepared in substantially the same way and using the bead beater having substantially the same glass beads as described in the previous examples. The bead beater is operated at a rotary speed of 20,000 RPM for about 3 minutes to lyse the sample.

In this example, amplification and detection of spiked DNA is performed on the StepOnePlus™ Real-Time PCR System from Applied Biosystems with the PremixExTaq (Probe qPCR) from TaKaRa (cat. RR390A), according to the manufacturer's instructions. 1.5 µL of prepared lysate is added directly to a qPCR reaction consisting of 1× Premix Ex Taq (contains TaKaRa Ex Taq HS, dNTP Mixture, $Mg^{2+}$, and Tli RNaseH), 1×ROX reference dye, 0.50 µM of each SpoA *Bacillus subtilis*-specific primer, 0.20 µM of SpoOA Taq- Man® probe (See table 1, Example 1) and 0.2 mg/mL BSA; in a final volume of 15 μL. In parallel, DNA without processing is tested as a positive control (at the same concentration). 1.5 μL of distilled water is also added to a qPCR reaction as a negative control.

Figure 14:
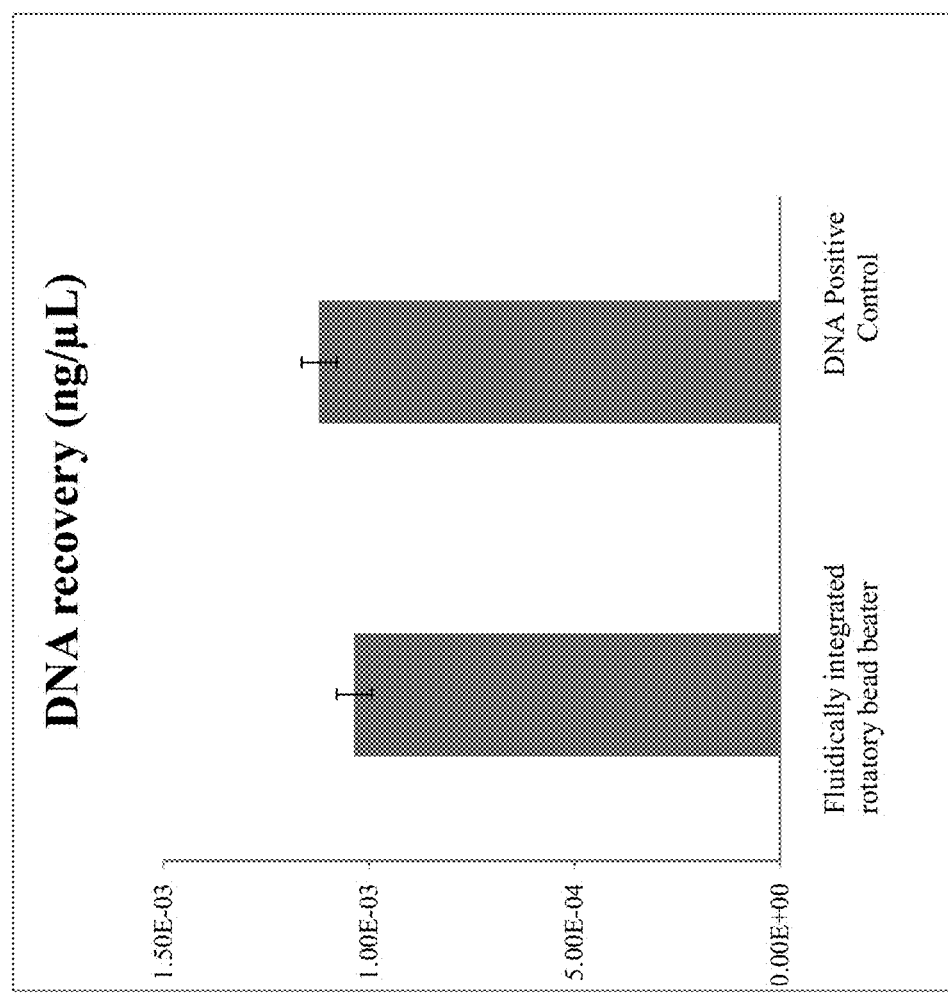
FIG. 14 is a graph of recovered DNA from *Bacillus subtilis* vegetative cells.

Table 2 provides the results of the recovered DNA concentration from the bead beater lysing vs. the positive control. The negative control samples indicated that no DNA was present. Ct values are also given for both lysing methods. FIG. 14 illustrates a graph of the average DNA recovered using the bead beater compared to the positive control. DNA recovery after mechanical lysis with the fluidically integrated rotatory bead beater is comparable to the Positive Control (difference of about 7.6%.) No DNA degradation was observed after the fluidically integrated rotatory bead beater process.

TABLE 2

| Treatment | Ct Mean values | Average DNA conc from qPCR (ng/μL) | % Recovery |
|---|---|---|---|
| Spiked DNA-Fluidically integrated rotatory Bead beater | 30.20 | 1.04E−03 | 92.4 |
| DNA positive Control | 29.54 | 1.12E−03 | 100.0 |
| Negative Control | UND | UND | NA |

Example 4

DNA and RNA Extraction from *Bacillus subtilis* Vegetative Cells

This example experiment shows that RNA, suitable for cDNA synthesis and amplification by RT-qPCR, may be extracted from bacterial cells using the fluidically integrated rotatory bead beater. A volume of 3 mL of broth culture of *Bacillus subtilis* subsp. *spizizenii* (ATCC 6633) vegetative cells in mid-log phase of growth (O.D550=0.60-0.70) is centrifuged and the pellet is re-suspended in Tris-EDTA buffer to obtain a final *Bacillus subtilis* concentration of $1.5 \times 10^8$ CFU/mL. A $5 \times 10^4$ CFU/mL dilution is prepared in Tris-EDTA buffer to be used as a starting material in the fluidically integrated rotatory bead beater.

The bead beater is prepared with substantially the same glass beads as described in the previous examples and loaded with a 200 μL vegetative cells dilution re-suspended in 200 μL Tris-EDTA buffer 1×. The bead beater is operated at a rotary speed of 20,000 RPM for about 3 minutes to lyse the sample.

Purification from the *Bacillus subtilis* lysates is performed in this example with two different commercial purification kits from Norgen (RNA/DNA/Protein Purification Kit) and Fermentas (GeneJET Viral DNA/RNA Purification Kit). Amplification and detection of RNA and DNA from *Bacillus subtilis* vegetative cells is performed on the StepOnePlus™ Real-Time PCR System from Applied Biosystems with the one Step PrimeScript™ RT-PCR kit (Perfect Real Time) from Takara (cat. RR064A), according to the manufacturer's instructions. 2.0 μL of prepared lysate is added directly in two RT-qPCR mixtures, with or without reverse transcriptase enzyme (PrimeScript RT enzyme Mix II), to detect RNA and DNA. Final mixtures consist of 1× One Step RT-PCR buffer III (includes dNTP Mixture, $Mg^{2+}$), 0.1 U/μL TaKaRa exTaq HS, 1× PrimeScript RT enzyme Mix II (in the RT+ mix), 1×ROX reference dye, 0.38 μM of each SpoA *Bacillus subtilis*-specific primer and 0.15 μM of SpoOA TaqMan® probe (See table 1 of Example 1); in a final volume of 20 μL. In parallel, vegetative cells without processing are tested as untreated controls (at the same concentrations). 2.0 μL of distilled water is also added to RT-qPCR (+RT enzyme) reactions as a negative control. The first step is 5 min at 42° C. for the reverse transcription (cDNA synthesis). The optimal cycling conditions for maximum sensitivity and specificity are 10 seconds at 95° C. for initial denaturation, then forty cycles of two steps being 1 second at 95° C. and 10 seconds at 60° C. Amplification was monitored during each elongation cycle by measuring the level of fluorescence. DNA and RNA concentrations are also calculated by interpolating Ct values in their corresponding calibration curves.

Figure 15:
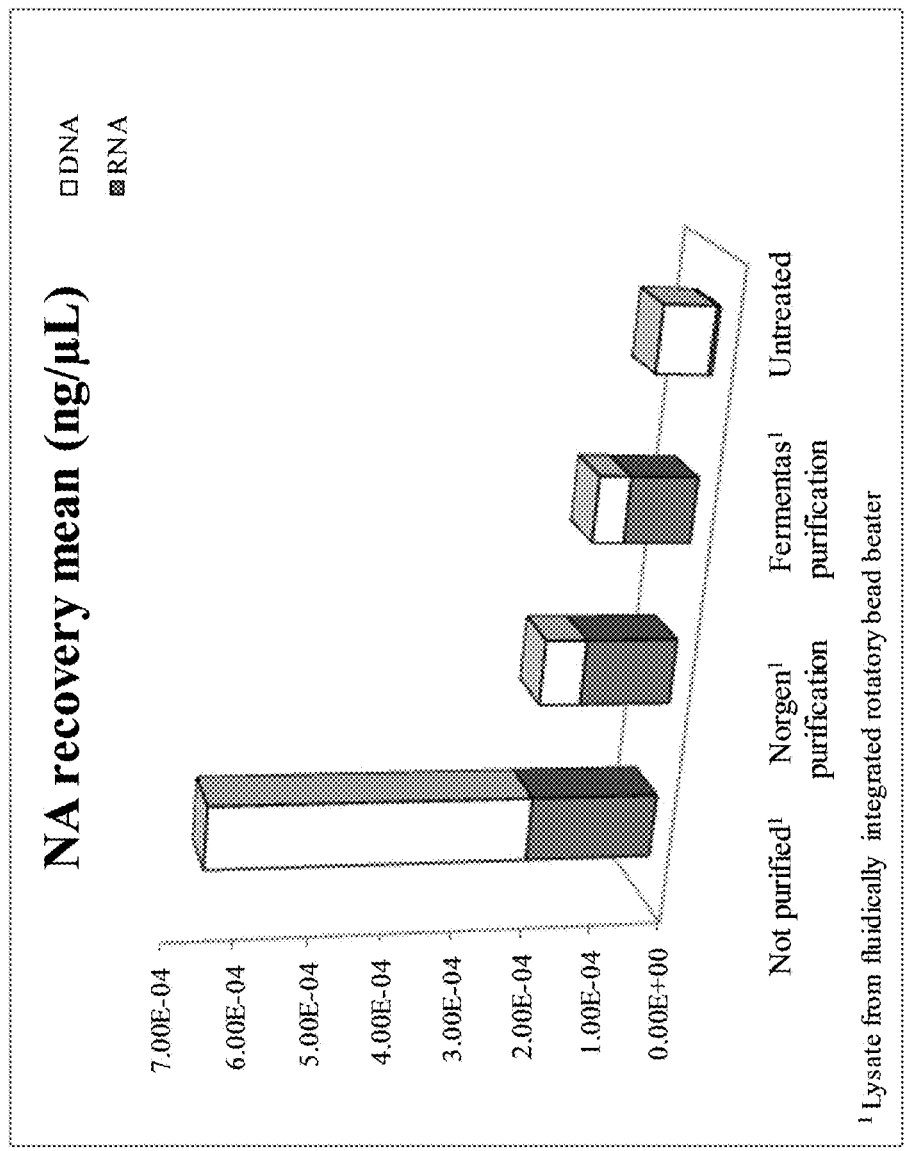
FIG. 15 is a graph of measured DNA and RNA concentration from *Bacillus subtilis* vegetative cells.

FIG. 15 shows a graphical presentation of RNA and DNA recovery mean concentrations (ng/μL) at different tested conditions: From NA lysate after fluidically integrated rotatory bead beater, from NA lysate after fluidically integrated rotatory bead beater and purification with the Norgen purification kit, from NA lysate after fluidically integrated rotatory bead beater and purification with the Fermentas purification kit and from the untreated *B. subtilis* re-supension. Results are a mean of 15 replicates at each concentration. Nucleic acid recovery in terms of DNA and RNA concentrations increased after mechanical lysis with the fluidically integrated rotatory bead beater, compared to the untreated condition, especially with regards to RNA recovery. After nucleic acid purification, the % NA recovery decreased (25-30% vs the not purified condition) due to the membrane purification process.

Example 5

RNA Recovery Comparison for *Bacillus subtilis* Vegetative Cells

In this example, RNA control is extracted from *B. subtilis* subsp. *spizizenii* (ATCC 6633) vegetative cells using the Norgen RNA/DNA/Protein Purification Kit. For each sample, 9.00 ng RNA are spiked in 800 μL of a buffered solution which also includes a chelating agent (Tris-EDTA buffer 1×, nucleases free from SIGMA).

In parallel, a lysis protocol is performed on the *Bacillus subtilis* vegetative cells prepared in substantially the same way and using the bead beater having substantially the same glass beads as described in the previous examples. The bead beater is operated at a rotary speed of 20,000 RPM for about 3 minutes to lyse the sample.

In this example, amplification and detection of spiked RNA is performed on the StepOnePlus™ Real-Time PCR System from Applied Biosystems with the one Step PrimeScript™ RT-PCR kit (Perfect Real Time) from TaKaRa (cat. RR064A), according to the manufacturer's instructions. 2.0 μL of prepared lysate is added directly to a RT-qPCR reaction consisting of 1× One Step RT-PCR buffer III (includes dNTP Mixture, $Mg^{2+}$), 0.1 U/μL TaKaRa exTaq HS, 1× PrimeScript RT enzyme Mix II, 1×ROX reference dye, 0.38 μM of each SpoA *Bacillus subtilis*-specific primer and 0.15 μM of SpoOA TaqMan® probe (See table 1 of Example 1); in a final volume of 20 μL. In parallel, RNA without processing is tested as a positive control (at the same concentration). 2.0 μL of distilled water is also added to a RT-qPCR reaction as a negative control.

Figure 16:
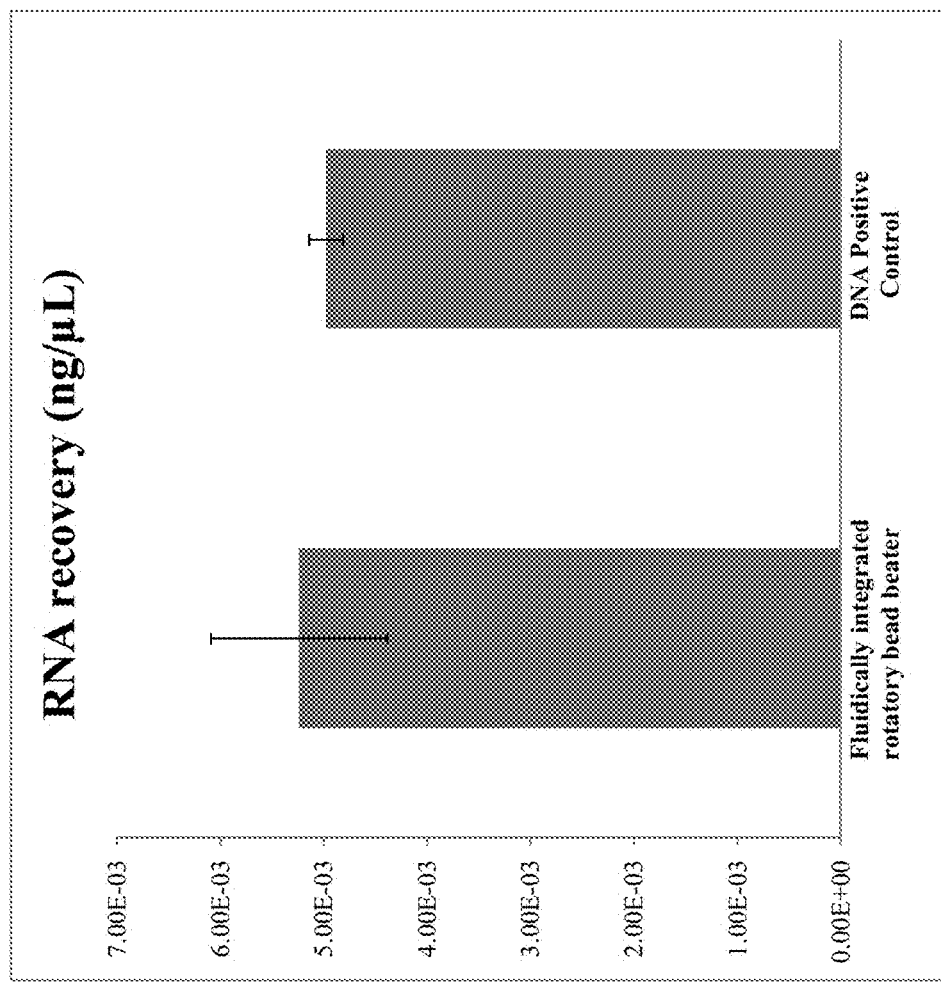
FIG. 16 is a graph of RNA recovery from *Bacillus subtilis* vegetative cells.
Figure 17A:
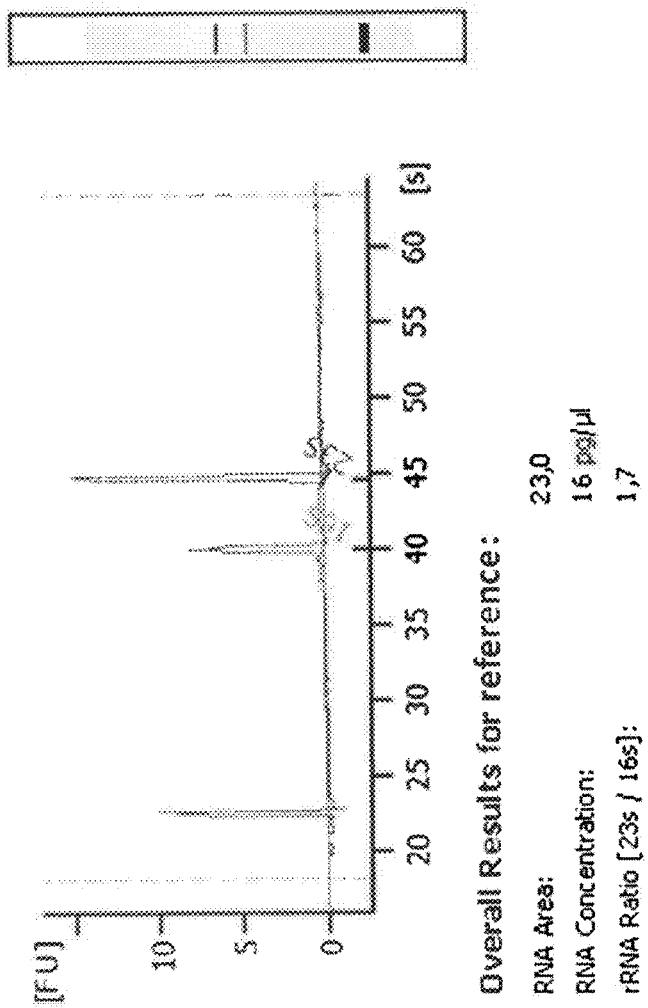

Table 3 provides the results of the recovered RNA concentration from the bead beater lysing vs. the positive control. The negative control samples indicated that no RNA was present. Ct values (number of PCR cycles needed to produce a positive signal) are also given for both lysing methods. FIG. 16 illustrates a graph of the average RNA recovered using the bead beater compared to the positive control. RNA recovery after mechanical lysis with the fluidically integrated rotatory bead beater is comparable to the Positive Control (difference of about 5.3%.) No RNA degradation was observed after the fluidically integrated rotatory bead beater process.

TABLE 3

| Treatment | Ct Mean values | Average RNA Conc from qPCR (ng/μL) | % Recovery |
|---|---|---|---|
| Spiked RNA-Fluidically integrated rotatory Bead beater | 30.04 | 5.24E−03 | 105.3 |
| RNA positive Control | 30.10 | 4.98E−03 | 100.0 |
| Negative Control | UND | UND | NA |

Example 6

RNA Integrity Analysis

In this example, an Agilent bioanalyzer with an associated LabChip® Kit provides a particularly effective method for evaluating total RNA integrity. The Agilent 2100 Bioanalyzer is a microfluidics-based platform for sizing, quantification and quality control of DNA, RNA, proteins and cells. It can be used to look at total RNA quality by observing the 16S and 23S ribosomal peaks of prokaryotes and their ratio. The ratio of the areas beneath the 23S:16S peaks is a measure of RNA purity, and it should fall in the range of 1.5-2.0.

RNA samples (1 μL) from untreated RNA and fluidically integrated rotatory bead beater nucleic acid lysates are run on the Agilent 2100 Bioanalyzer using Agilent RNA 6000 Pico Kit (cat #5067-1513) and Agilent RNA 6000 Nano Kit (cat #5067-1511) for the analysis of total RNA (eukaryotic and prokaryotic) and mRNA samples. FIG. 16A provides the Bioanalyzer rRNA profile for the untreated RNA control (reference), while FIGS. 16B and 16C provide the Bioanalyzer rRNA profiles for two different samples lysed with the rotary bead beater. As is observed, the rRNA ratios in the two examples of nucleic acid samples processed in the fluidically integrated rotatory bead beater are within specifications (1.5-2.0), meaning that the RNA integrity is correct. The 23S and 16S peaks from the bead beater samples are noticeably smaller than the control sample. This is because the lysates are a mix of RNA and DNA and the presence of DNA in the bead beater samples affects the Agilent bioanalyzer electropherogram resolution.

The foregoing description of the specific embodiments and examples will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

Embodiments of the present invention have been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The Summary and Abstract sections may set forth one or more but not all exemplary embodiments of the present invention as contemplated by the inventor(s), and thus, are not intended to limit the present invention and the appended claims in any way.

The breadth and scope of the present invention should not be limited by any of the above-described exemplary embodiments, but should be defined only in accordance with the following claims and their equivalents.

What is claimed is:

1. A system for at least one of homogenization and lysis of a sample, comprising:
  a disposable housing configured to be removably coupled to an analyzer, the disposable housing comprising:
    a first reservoir;
    a second reservoir;
    one or more walls forming an enclosed chamber having an inlet and a plurality of fluidic connections, wherein at least one of the one or more walls of the enclosed chamber comprise a thermally controllable surface;
    a first fluidic network coupled to at least one of the plurality of fluidic connections and configured to introduce at least the sample to the enclosed chamber from the first reservoir;
    a second fluidic network coupled to at least one of the plurality of fluidic connections and configured to expel at least the sample from the enclosed chamber to the second reservoir; and
    a rotary element disposed within the enclosed chamber.

2. The system of claim 1, wherein the one or more walls form a substantially cylindrical enclosed chamber.

3. The system of claim 1, wherein the one or more walls form an enclosed chamber having a rectangular cross section.

4. The system of claim 1, wherein the inlet is configured to introduce solid, semi-solid, or liquid samples from an external environment.

5. The system of claim 1, wherein the inlet is located at the top of the enclosed chamber.

6. The system of claim 1, wherein the inlet is located on the side of the enclosed chamber.

7. The system of claim 1, further comprising a lid configured to fit over the inlet and prevent leakage.

8. The system of claim 1, wherein at least a portion of either the first fluidic network or the second fluidic network is configured to pressurize or depressurize the chamber.

9. The system of claim 1, further comprising a third fluidic network coupled to the enclosed chamber and configured to pressurize or depressurize the chamber.

10. The system of claim 1, further comprising a plurality of beads disposed within the chamber.

11. The system of claim 10, wherein the plurality of beads comprise materials selected from the group being plastic, glass, ceramic, and silica.

12. The system of claim 10, wherein the plurality of beads range in diameter from 1 micron to approximately 3000 microns.

13. The system of claim 10, wherein the rotary element is configured to excite the plurality of beads.

14. The system of claim 1, further comprising an actuator coupled to the rotary element and configured to rotate the rotary element about an axis extending along a length of the rotary element.

15. The system of claim 14, wherein the actuator is detachably coupled to the rotary element via a coupling mechanism.

16. The system of claim 15, further comprising a support disposed substantially at the coupling mechanism and configured to prevent leakage.

17. The system of claim 1, further comprising a cavity disposed on a side of the enclosed chamber, such that a heated surface placed against the cavity substantially raises the temperature within the enclosed chamber.

18. A system for performing molecular testing, comprising:
a disposable housing configured to be removably coupled to an analyzer, the disposable housing comprising:
one or more fluid chambers;
a fluidic network connecting at least the one or more fluid chambers to a movable central chamber; and
a device comprising:
one or more walls forming an enclosed chamber having an inlet and a plurality of fluidic connections, at least a portion of which are coupled to the fluidic network, wherein at least one of the one or more walls of the enclosed chamber comprise a thermally controllable surface, and
a rotary element disposed within the enclosed chamber.

19. The system of claim 18, wherein the one or more walls form a substantially cylindrical enclosed chamber.

20. The system of claim 18, wherein the one or more walls form an enclosed chamber having a rectangular cross section.

21. The system of claim 18, wherein the inlet is configured to introduce solid, semi-solid, or liquid samples from an external environment.

22. The system of claim 18, wherein the inlet is located at the top of the enclosed chamber.

23. The system of claim 18, wherein the inlet is located on a side of the enclosed chamber.

24. The system of claim 18, further comprising a lid configured to fit over the inlet and prevent leakage.

25. The system of claim 18, wherein at least a portion of the fluidic network is configured to pressurize or depressurize the enclosed chamber.

26. The system of claim 18, further comprising a plurality of beads disposed within the enclosed chamber.

27. The system of claim 26, wherein the plurality of beads comprise materials selected from the group being plastic, glass, ceramic, and silica.

28. The system of claim 26, wherein the plurality of beads range in diameter from 1 micron to approximately 3000 microns.

29. The system of claim 26, wherein the rotary element is configured to excite the plurality of beads.

30. The system of claim 18, further comprising an actuator coupled to the rotary element and configured to rotate the rotary element about an axis extending along a length of the rotary element.

31. The system of claim 30, wherein the actuator is detachably coupled to the rotary element via a coupling mechanism.

32. The system of claim 31, wherein the device further comprises a support disposed substantially at the coupling mechanism and configured to prevent leakage.

33. A system for performing molecular testing, comprising:
a housing comprising:
one or more fluid chambers;
a fluidic network connecting at least the one or more fluid chambers to a movable central chamber; and
a device comprising:
one or more walls forming an enclosed chamber having an inlet and a plurality of fluidic connections, at least a portion of which are coupled to the fluidic network, wherein at least one of the one or more walls of the enclosed chamber comprise a thermally controllable surface,
a rotary element disposed within the enclosed chamber, and
a cavity disposed on a side of the enclosed chamber, such that a heated surface placed against the cavity substantially raises the temperature within the enclosed chamber.

34. A method for lysing a sample, comprising:
introducing at least the sample into an enclosed chamber via a fluidic connection coupled to a fluidic network that is further coupled to one or more other chambers, wherein one or more walls of the enclosed chamber comprises a thermally controllable surface, wherein the enclosed chamber, the fluidic connection, the fluidic network, and the one or more other chambers are disposed within a disposable housing removably coupled to an analyzer;
rotating a rotary element, disposed within the enclosed chamber, along an axis extending along a length of the rotary element; and
lysing the sample within the enclosed chamber via the movement of the rotary element.

35. The method of claim 34, further comprising expelling at least the sample from the enclosed chamber via another fluidic connection coupled to the fluidic network.

36. The method of claim 34, further comprising pressurizing or depressurizing the enclosed chamber via the fluidic network.

37. The method of claim 34, further comprising attaching an actuator to the rotary element via a coupling mechanism.

38. The method of claim 34, further comprising introducing at least the sample into the enclosed chamber via an inlet configured to introduce samples from an external environment.

39. The method of claim 38, wherein introducing at least the sample via the inlet comprises introducing solid, semi-solid, or liquid samples.

40. The method of claim 34, further comprising heating the sample via a cavity disposed on a side of the enclosed chamber.

41. A method for lysing a sample, comprising:
introducing at least the sample into an enclosed chamber via a fluidic connection coupled to a fluidic network that is further coupled to one or more other chambers, wherein one or more walls of the enclosed chamber comprises a thermally controllable surface, wherein the enclosed chamber, the fluidic connection, the fluidic network, and the one or more other chambers are disposed within a disposable housing removably coupled to an analyzer;
rotating a rotary element, disposed within the enclosed chamber, along an axis extending along a length of the rotary element;
exciting a plurality of beads disposed within the enclosed chamber by the movement of the rotary element; and
lysing the sample within the enclosed chamber via the movement of the rotary element and the plurality of beads.

42. The method of claim 41, further comprising expelling at least the sample from the enclosed chamber via another fluidic connection connected to the fluidic network.

43. The method of claim 41, further comprising pressurizing or depressurizing the enclosed chamber via the fluidic network.

44. The method of claim 41, further comprising attaching an actuator to the rotary element via a coupling mechanism.

45. The method of claim 41, further comprising introducing at least the sample into the enclosed chamber via an inlet configured to introduce samples from an external environment.

46. The method of claim 45, wherein introducing at least the sample via the inlet comprises introducing solid, semi-solid, or liquid samples.

47. The method of claim 41, further comprising heating the sample via a cavity disposed on a side of the enclosed chamber.

48. A method for homogenizing a sample, comprising:
introducing at least the sample into an enclosed chamber via a fluidic connection coupled to a fluidic network that is further coupled to one or more other chambers, wherein one or more walls of the enclosed chamber comprises a thermally controllable surface, wherein the enclosed chamber, the fluidic connection, the fluidic network, and the one or more other chambers are disposed within a disposable housing removably coupled to an analyzer;
rotating a rotary element, disposed within the enclosed chamber, along an axis extending along a length of the rotary element; and
homogenizing the sample within the enclosed chamber via the movement of the rotary element.

49. The method of claim 48, further comprising expelling at least the sample from the enclosed chamber via another fluidic connection coupled to the fluidic network.

50. The method of claim 48, further comprising pressurizing or depressurizing the enclosed chamber via the fluidic network.

51. The method of claim 48, further comprising attaching an actuator to the rotary element via a coupling mechanism.

52. The method of claim 48, further comprising introducing at least the sample into the enclosed chamber via an inlet configured to introduce samples from an external environment.

53. The method of claim 52, wherein introducing at least the sample via the inlet comprises introducing solid, semi-solid, or liquid samples.

54. The method of claim 48, further comprising heating the sample via a cavity disposed on a side of the enclosed chamber.

55. A method for homogenizing a sample, comprising:
introducing at least the sample into an enclosed chamber via a fluidic connection coupled to a fluidic network that is further coupled to one or more other chambers, wherein one or more walls of the enclosed chamber comprises a thermally controllable surface, wherein the enclosed chamber, the fluidic connection, the fluidic network, and the one or more other chambers are disposed within a disposable housing removably coupled to an analyzer;
rotating a rotary element, disposed within the enclosed chamber, along an axis extending along a length of the rotary element;
exciting a plurality of beads disposed within the enclosed chamber by the movement of the rotary element; and
homogenizing the sample within the enclosed chamber via the movement of the rotary element and the plurality of beads.

56. The method of claim 55, further comprising expelling at least the sample from the enclosed chamber via another fluidic connection coupled to the fluidic network.

57. The method of claim 55, further comprising pressurizing or depressurizing the enclosed chamber via the fluidic network.

58. The method of claim 55, further comprising attaching an actuator to the rotary element via a coupling mechanism.

59. The method of claim 55, further comprising introducing at least the sample into the enclosed chamber via an inlet configured to introduce samples from an external environment.

60. The method of claim 59, wherein introducing at least the sample via the inlet comprises introducing solid, semi-solid, or liquid samples.

61. The method of claim 55, further comprising heating the sample via a cavity disposed on a side of the enclosed chamber.

* * * * *

UNITED STATES PATENT AND TRADEMARK OFFICE
CERTIFICATE OF CORRECTION

| | | |
|---|---|---|
| PATENT NO. | : 9,304,066 B2 | Page 1 of 1 |
| APPLICATION NO. | : 13/836741 | |
| DATED | : April 5, 2016 | |
| INVENTOR(S) | : Carrera Fabra et al. | |

It is certified that error appears in the above-identified patent and that said Letters Patent is hereby corrected as shown below:

Title Page

Item 54. Please replace "BEADER" with --BEATER--.

Specification

Column 1, Line 2. Please replace "BEADER" with --BEATER--.

Column 7, Line 45. Please replace "fits 406" with --frits 406--.

Signed and Sealed this
Seventh Day of June, 2016

Michelle K. Lee
*Director of the United States Patent and Trademark Office*